United States Patent
Igarashi et al.

(10) Patent No.: US 11,607,375 B2
(45) Date of Patent: Mar. 21, 2023

(54) OIL-IN-WATER TYPE EMULSION AND METHOD FOR PRODUCING OIL-IN-WATER TYPE EMULSION

(71) Applicant: WACKER CHEMIE AG, Munich (DE)

(72) Inventors: Kenji Igarashi, Ibaraki (JP); Mikiko Kimura, Ibaraki (JP)

(73) Assignee: WACKER CHEMIE AG, Munich (DE)

( * ) Notice: Subject to any disclaimer, the term of this patent is extended or adjusted under 35 U.S.C. 154(b) by 79 days.

(21) Appl. No.: 17/057,295

(22) PCT Filed: May 17, 2019

(86) PCT No.: PCT/EP2019/062851
§ 371 (c)(1),
(2) Date: Nov. 20, 2020

(87) PCT Pub. No.: WO2019/224123
PCT Pub. Date: Nov. 28, 2019

(65) Prior Publication Data
US 2021/0346247 A1   Nov. 11, 2021

(30) Foreign Application Priority Data

May 21, 2018   (JP) .............................. JP2018-096768

(51) Int. Cl.
*A61K 8/06*   (2006.01)
*A61K 8/25*   (2006.01)
(Continued)

(52) U.S. Cl.
CPC ................ *A61K 8/062* (2013.01); *A61K 8/25* (2013.01); *A61K 8/897* (2013.01); *C09C 1/3081* (2013.01);
(Continued)

(58) Field of Classification Search
CPC .......... A61K 8/062; A61K 8/25; A61K 8/897; A61K 2800/10; A61K 8/00; A61K 8/0275;
(Continued)

(56) References Cited

U.S. PATENT DOCUMENTS 4,119,712 A * 10/1978 Goldner ................... A61K 8/06
424/69
2003/0175221 A1   9/2003 Gers-Barlag et al.
(Continued)

FOREIGN PATENT DOCUMENTS

CN   107109061 A   8/2017
EP   1526153 A1   10/2014
(Continued)

OTHER PUBLICATIONS

JP 2019030866, English Abstract.
(Continued)

*Primary Examiner* — Anthony J Zimmer
(74) *Attorney, Agent, or Firm* — Brooks Kushman P. C.

(57) ABSTRACT

An oil-in-water type emulsion is characterized in that a fumed silica particle group in which lower order aggregates are aggregated with each other to form a higher order aggregate by a non-chemical bond forms a network-like surrounding structure including an oil inside the network-like surrounding structure.

6 Claims, 2 Drawing Sheets

Part A

Details of Part A

(51) Int. Cl.
  *A61K 8/897* (2006.01)
  *C09C 1/30* (2006.01)
  *C09K 23/00* (2022.01)

(52) U.S. Cl.
  CPC ........ *C09K 23/002* (2022.01); *A61K 2800/10* (2013.01); *C01P 2006/12* (2013.01)

(58) Field of Classification Search
  CPC ...... A61K 8/06; C09C 1/3081; C09K 23/002; C01P 2006/12; A61Q 19/00
  See application file for complete search history.

(56) References Cited

U.S. PATENT DOCUMENTS

| | | |
|---|---|---|
| 2004/0131527 A1 | 7/2004 | Gottschalk-Gaudig et al. |
| 2005/0107520 A1 | 5/2005 | Gottschalk-Gaudig et al. |
| 2007/0209552 A1 | 9/2007 | Gottschalk-Gaudig |
| 2020/0261334 A1 | 8/2020 | Sengoku et al. |

FOREIGN PATENT DOCUMENTS

| | | |
|---|---|---|
| JP | 2000095632 A | 4/2000 |
| JP | 2004203735 A | 7/2004 |
| JP | 2008031487 A | 2/2008 |
| JP | 6312234 B1 | 4/2018 |
| JP | 6344878 B1 | 6/2018 |
| JP | 2019030866 A | 2/2019 |
| WO | 2006018112 A1 | 2/2006 |
| WO | 16102384 A1 | 6/2016 |
| WO | 2019030853 A1 | 2/2019 |

OTHER PUBLICATIONS

Journal of the Japan Society of Colour Material, 2016, vol. 89, No. 6, pp. 203-206, English Abstract.
B. P. Binks et al., "Transitional Phase Inversion of Solid-Stabilized Emulsions Using Particle Mixtures" Langmuir, Apr. 1, 2000, vol. 16, No. 8, pp. 3748-3756, US, XP055610720, ISSN: 0743-7463, DOI: 10.1021/la991427q.
S. Komura et al., "Adsorption of Colloidal Particles to Curved Interfaces", The Journal of Chemical Physics, Jun. 27, 2006, vol. 124, p. 241104, DOI: 10.1063/1.2216697.
Sebastien Simon et al., "Rheological Properties of Particle-Stabilized Emulsions", Journal of Dispersion Science and Technology, 2010, vol. 31, No. 5, pp. 632-640, XP002793355, DOI: 10.1080/01932690903218062.
Tomoyuki Suzuki: Master Thesis, Department of Chemistry for Materials, 2010, Faculty of Engineering Graduate School of Engineering, Mie University.
Yoshimune Nonomura, "Pickering Emulsions", Journal of the Japan Society of Colour Material, 2016, vol. 89, No. 6, pp. 203-206.

\* cited by examiner

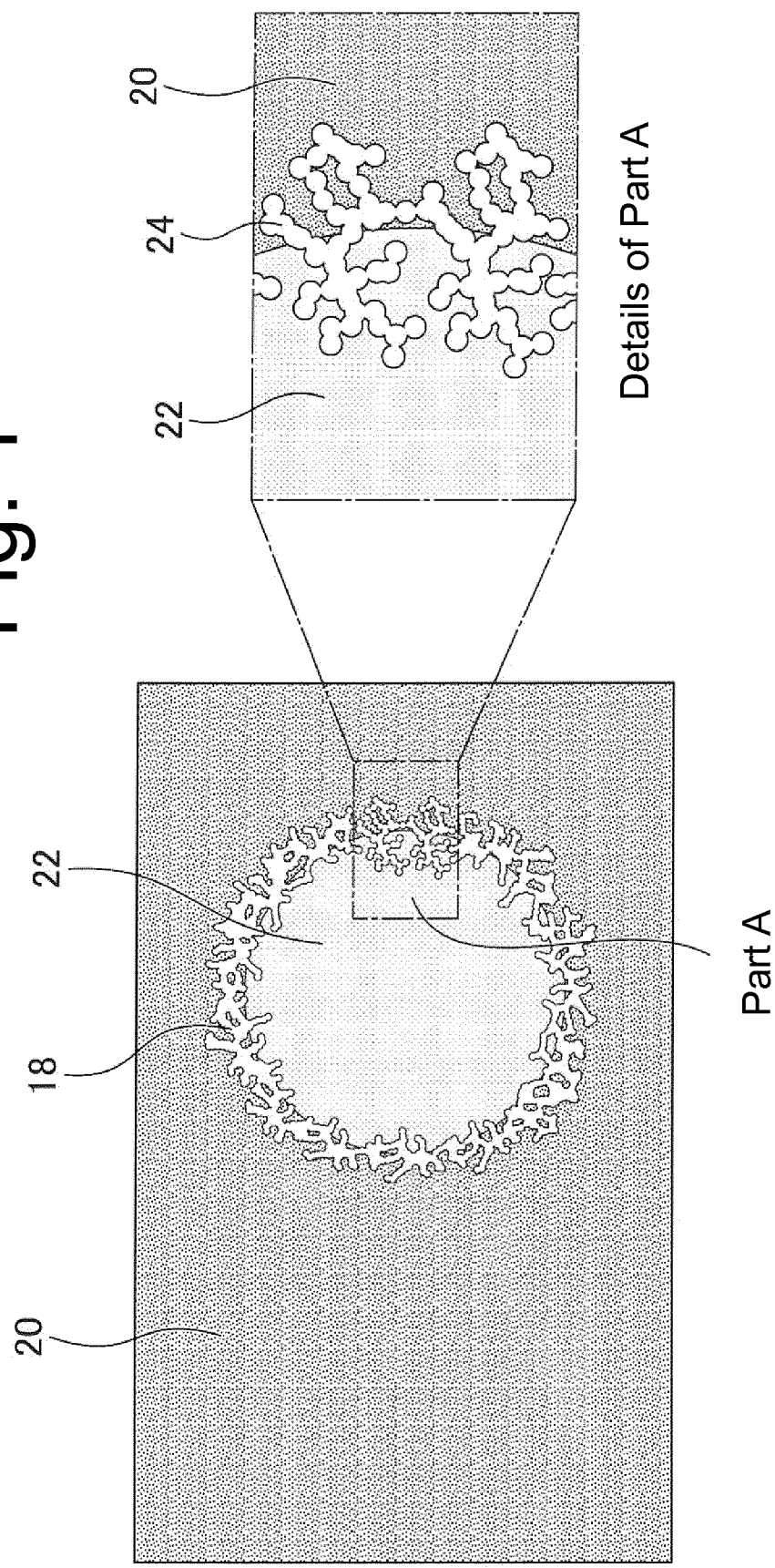

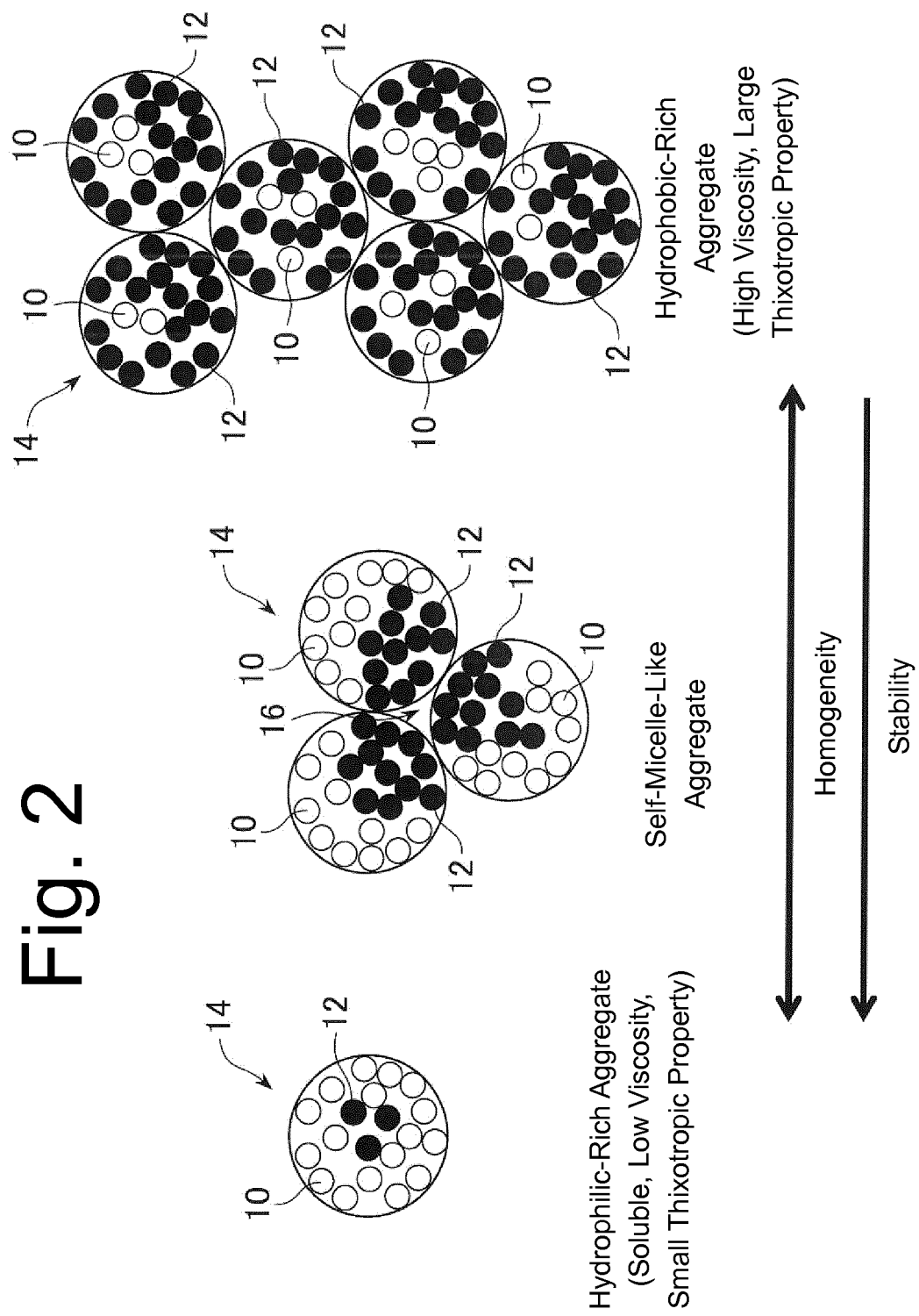

OIL-IN-WATER TYPE EMULSION AND METHOD FOR PRODUCING OIL-IN-WATER TYPE EMULSION

CROSS REFERENCE TO RELATED APPLICATIONS

This application is the U.S. National Phase of PCT Appln. No. PCT/EP2019/062851 filed May 17, 2019, which claims priority to Japanese Application No. 2018-096768 filed May 21, 2018, the disclosures of which are incorporated in their entirety by reference herein.

BACKGROUND OF THE INVENTION

1. Field of the Invention

The present invention relates to an oil-in-water emulsion and a method for producing the oil-in-water emulsion, and more specifically, to an oil-in-water emulsion reliably having stability and a method for producing the oil-in-water emulsion.

2. Description of the Related Art

Aqueous dispersions, in which inorganic solid particles such as silica, titanium oxide, or the like are dispersed in water to obtain an emulsion, a suspension, or the like, are conventionally known and widely used as a rheology control agent and a compounding agent to be added to a cosmetic. In these aqueous dispersions including the inorganic particles, the inorganic particles are not dissolved in water. This is exactly the reason why stability, meaning that the inorganic particles in the dispersed state do not precipitate for a long period of time, and are uniformity dispersed, meaning the absence of local unevenness in the aqueous dispersion, are important.

In particular, in a case where fumed silica is used as the inorganic particles, if the fumed silica is hydrophobic silica, the aqueous dispersion is thickened and imparted with a thixotropic property. If the aqueous dispersion becomes excessively thickened, instability such as precipitation of the hydrophobic silica particles may be exhibited. On the other hand, if the fumed silica is hydrophilic silica, the hydrophilic silica is dissolved in water and thus can achieve stability in this sense, however, the hydrophilic silica is unsuitable for applications requiring a high viscosity as the aqueous dispersion.

As described above, required characteristics of the aqueous dispersion vary in accordance with its applications; however, it has been technically difficult to achieve both the required characteristics, and the stability and the uniformity of the aqueous dispersion.

Regarding this point, Japanese Patent Application Laid-Open No. 2004-2037354 discloses that in an aqueous dispersion including silica as the inorganic particles, the stability in the sense of preventing precipitation of silica over a lapse of time can be improved in the aqueous dispersion including the silica by focusing on a contact angle of the silica in a bulk state and thereby optimizing the contact angle.

However, Japanese Patent Application Laid-Open No. 2004-2037354 fails to disclose, not only whether the stability in the dispersion state is achieved, but also whether the uniformity in the dispersion state is achieved. Needless to say, there is no suggestions as to whether characteristics required for the aqueous dispersion, and the stability and the uniformity of the aqueous dispersion can be simultaneously achieved.

On the other hand, regarding an emulsion as one type of the dispersion, in an emulsified state of a solid phase or a liquid phase with a liquid phase, a technique for forming an emulsified state using a surfactant is known. For the emulsion, similar to the aqueous dispersion, the stability in the emulsified state in the sense of preventing separation between the solid or liquid dispersed phase, and the liquid continuous phase with the lapse of time, is essentially important.

In Japanese Patent Application Laid-Open No. 2000-095632, in particular, as a Pickering emulsion in which an inorganic particle is used as a substitute for a surfactant, a product in which various oily components are emulsified with titanium oxide particles is used for cosmetic applications and the like.

Further, Japanese Patent Application Laid-Open No. 2008-031487 shows a Pickering emulsion in which a silicone oil or other silicone substances are emulsified with silica particles.

Such a Pickering emulsion takes a form of an oil-in-water emulsion in which a composite particle composed of an oil drop constituting a core and an inorganic particle present on a surface of the oil drop which is an interface between an oil phase and an aqueous phase exists in an emulsified state in the aqueous phase as a composite particle group.

Such a Pickering emulsion has advantages in that an adverse effect caused by an environmentally harmful organic surfactant is eliminated by forming the emulsion without using the organic surfactant and the silica serving as a functional agent can be provided in an aqueous system, not as a particle, and thus, development of a wide range of applications in medicines, foods, defoaming agents, and the like has been expected as an oil-in-water type emulsion.

In such a Pickering emulsion, J. Jpn. Soc. Colour Mater., 89(6), 203 (2016), Chem. Phys., 124, 241104 (2006), and Japanese Patent Application Laid-Open No. 2008-031487 indicate that, regarding the inorganic particle as a substitute for the surfactant, the balance between hydrophobicity and hydrophilicity of the inorganic particle present at the interface is important to achieve the stability of the Pickering emulsion.

However, the conventional Pickering emulsion has the following technological problems.

First, the stability in the emulsified state in the sense of preventing separation between the solid or liquid dispersed phase, and the liquid continuous phase with the lapse of time is not sufficiently achieved.

More specifically, J. Jpn. Soc. Colour Mater., 89(6), 203 (2016) and J. Chem. Phys., 124, 241104 (2006) only construct a simplified model in which a spherical particle exists at the interface between a liquid phase (e.g., an aqueous phase) and a liquid phase (e.g., an oil phase) to examine a Pickering emulsion model without considering how a timing of adding the inorganic particle and a shearing speed and shearing time for emulsification affect characteristics of the emulsion in a relationship between the aqueous phase and the liquid phase for forming the Pickering emulsion. Thus, a factor and mechanism that control the stability of the emulsion are hardly elucidated.

In particular, in a case where the silica is adopted as the inorganic particle, there is no reference to how a primary aggregate and a secondary aggregate formed due to an aggregation property of the silica affect the balance between hydrophobicity and hydrophilicity.

Regarding this point, in Suzuki, Tomoyuki (2010) Master's Thesis, Department of Chemistry for Materials, Faculty of Engineering Graduate School of Engineering, Mie University, attempts are made to change the characteristics of the emulsion by using hydrophobic silica used as the inorganic particle to adsorb a hydrophilic polymer surfactant on the surface of the hydrophobic silica thereby adjusting the balance between hydrophobicity and hydrophilicity.

However, in Suzuki, Tomoyuki (2010) Master's Thesis, Department of Chemistry for Materials, Faculty of Engineering Graduate School of Engineering, Mie University, the hydrophilic polymer surfactant is adsorbed only on the inorganic particle having the hydrophobic silica as a base using one type of the oil phase as a core, thus there is a problem in that the types of oil agents to be emulsified are limited. Even if the characteristics of the emulsion are affected by the balance between hydrophobicity and hydrophilicity, a method for adjusting the balance between hydrophobicity and hydrophilicity is complicated and costly. Thus, such a method is not established as a product designing method to commercialize the emulsion.

As such, an industrially designing method of the Pickering emulsion including the silica particle, conventionally, only a pretreatment for a degree of hydrophobicity of the silica is performed in a stage of a raw material to perform coating of the oil in an emulsification process by partially hydrophobizing silanol groups on the surface of the silica. It is still unknown which design parameter should be focused on in order to industrially produce the stable emulsion at a practical level.

Second, for example, a group of composite particles each having the silica particle on the surface (interface) of the oil drop constituting a core is isolated and produced by removing a water content after the formation of the Pickering emulsion. In the composite particle group, the silica particle used as the inorganic particle can be strongly bound to the core surface so as to coat the oil surface. Thus, the composite particle group is expected to be used in many applications, for example, in a case where it is advantageous to apply the silica particle as a functional agent and the core as a different functional agent to an application target as the composite particle as compared with a case where they are separately applied to the application target. However, a problem of variations between the composite particle groups has not been examined, yet.

More specifically, the composite particle includes, as its specification, a particle diameter, a coating layer thickness, a coating degree, and an embedding degree (a contact angle) of the silica particle into the core surface. The particle diameter, the coating layer thickness, and the coating degree are deeply related to a hardness of the composite particle, while the embedding degree of the silica particle into the core surface is deeply related to a binding degree between the silica particle and the core. Thus, variations in these specifications between the composite particle groups make it difficult to provide a reliable product.

Third, conventionally, little attention has been given to adjusting the particle diameter, the coating layer thickness, the coating degree, and the embedding degree (the contact angle) as the specifications of the composite particle in accordance with the application for forming the Pickering emulsion. More specifically, for example, in the cosmetic applications, the composite particle including a silicone rubber particle as the core is often adopted. Although the particle diameter and the coating layer thickness affect use feeling, a method for adjusting the particle diameter and the coating layer thickness has not yet been examined. More specifically, the composite particle having flexibility as a whole provides excellent fit feeling to the skin after the application; however, the composite particle is deformed during the application, thereby causing an increased contact area with the skin and an increased frictional resistance between the particles, resulting in reduction in stretchability of the composite particles on the skin. Thus, a technique for achieving such stretchability by softening the rubber particle as the core and, in the same time, hardening the silica coating layer constituting an outer shell is demanded.

Regarding the second and third points, it is known that fluorocarbon, in which a part of hydrogen atoms in hydrocarbon are substituted with fluorine atoms, is more excellent in stability, heat resistance, water resistance, oil resistance, and water repellency than normal organopolysiloxane, for example, dimethylpolysiloxane, and has a characteristic feature, such as oil repellency, which is not seen at all in the normal organopolysiloxane. Thus, it is expected that a substance obtained by introducing a structure of the fluorocarbon into the skeleton of organopolysiloxane (fluorine-containing organopolysiloxane) exhibits excellent characteristics in various applications in various forms such as an oil form, a rubber form, and a resin form and in various states such as a bulk state, a solution state, a dispersion state (or a suspension state), a coating state, and a granular state (or a powder state). However, it is currently extremely difficult to develop the applications in the granular state or the powder state.

This is because it is difficult to form a solution, dispersion, or suspension of the fluorine-containing organopolysiloxane using water or an organic solvent due to super water repellency or super oil repellency of the fluorine-containing organopolysiloxane. Since it is difficult to obtain the granular state or the powder state by evaporating the solvents in these solutions, the only alternative method includes the crushing or the like of the rubber or resin form. Thus, resulting granular materials or powders have irregular shapes with large variations in size.

Regarding this point, in Japanese Patent No. 6312234, the applicant of the present invention has found that, in the aqueous dispersion in which, like fumed silica particles, lower order aggregates in an inorganic particle group are aggregated each other to form a higher order aggregate by a non-chemical bond and dispersed in water and in an oil-in-water type Pickering emulsion prepared by adding an oil to such an aqueous dispersion as a base, there is a stability adjusting mechanism which involves exchange (rearrangement) or movement (orientation) at an aggregate level.

More specifically, the applicant of the present invention has found that, in the aqueous dispersion in which the lower order aggregates in the inorganic particle group are aggregated with each other to form a higher order aggregate by a non-chemical bond and dispersed in water, a hydrophilic-rich aggregate, a hydrophobic-rich aggregate, and their intermediate aggregate (a self-micelle-like aggregate) are produced by the exchange (the rearrangement) or the movement (the orientation) at the aggregate level and the self-micelle-like aggregate is important for the stability of the aqueous dispersion and the oil-in-water type Pickering emulsion prepared by adding the oil to such an aqueous dispersion as a base.

However, a relationship between a network structure formed by a high aggregation property of the fumed silica particle and the stability of the oil-in-water type Pickering emulsion, in particular, how the stability of the oil-in-water type Pickering emulsion is affected by the network structure formed by the same or different aggregates among the hydrophilic-rich aggregate, the hydrophobic-rich aggregate, and the self-micelle-like aggregate has not been examined. In particular, no investigation has been conducted to determine whether it is possible to form the oil-in-water type Pickering emulsion including the fluorine-containing organopolysiloxane having super water repellency or super oil repellency as the oil in the first place and, if so, what are the conditions for forming such an oil-in-water type Pickering emulsion. This implies that, according to the common general knowledge of a person skilled in the art at that time, it is not expected that the oil-in-water type Pickering emulsion including the fluorine-containing organopolysiloxane having super water repellency or super oil repellency as the oil can be formed.

In view of the above-described technical problems, an object of the present invention is to provide an oil-in-water type emulsion reliably having a stability and a method for producing the oil-in-water type emulsion.

In view of the above-described technical problems, an object of the present invention is to provide a method for forming a granular material or powder including fluorine-containing organopolysiloxane, having a regular shape and small variations in size.

SUMMARY OF THE INVENTION

It has now been found, that when a fumed silica particle group forms a network due to a high aggregation property of the fumed silica particle, the fumed silica particle group forms a three-dimensional surrounding structure forming a space inside thereof instead of a planar structure, and setting, in accordance with the aggregation property of the fumed silica particle, the total molar ratio represented by the total number of moles of surface hydrophilic groups of the entire silica particle groups obtained from each of the fumed silica particle groups/the total number of moles of surface hydrophobic groups of the entire fumed silica particle groups obtained from each of the fumed silica particle groups to a predetermined lower limit value or more and/or a predetermined upper limit value or less determines which aggregate, a self-micelle-like aggregate, a hydrophobic-rich aggregate, or a hydrophilic-rich aggregate, is primarily produced, and, as a result thereof, it now becomes possible to provide an aqueous dispersion in accordance with a purpose, such as imparting viscosity and a thixotropic property. Further, the self-micelle-like aggregate in particular has excellent stability and homogeneity.

BRIEF DESCRIPTION OF THE DRAWINGS

FIG. 1 is a schematic diagram illustrating a network-like surrounding structure in which oil is surrounded by aggregates of a fumed silica group.

FIG. 2 is a schematic diagram illustrating types of aggregates obtained when fumed silica particles are dispersed in water in Examples. A size of each aggregate itself is exaggerated for the sake of clarity.

DETAILED DESCRIPTION OF THE PREFERRED EMBODIMENTS

In the case where fumed silica is used as the inorganic particle, a self-micelle-like aggregate-rich aqueous dispersion can be produced by setting the total mole number ratio within a range of 20/80 to 80/20 in a stage of a raw material of the silica.

Further, when obtaining an oil-in-water type emulsion (a Pickering emulsion) by coating an oil drop with the self-micelle aqueous dispersion including the fumed silica particle, variations in a degree of hydrophobicity between composite particles can be reduced by applying a shearing speed of a predetermined value or more, primarily in a stage of the aqueous dispersion and thereby promoting rearrangement of primary aggregates between secondary aggregates and/or orientation of the primary aggregates in the secondary aggregates, and as a result thereof, the more stable and homogenous oil-in-water type emulsion can be produced.

The present invention has been made in view of the foregoing discussion. That is, the oil-in-water type emulsion and the production and design methods of the oil-in-water type emulsion of the present invention are:

(1) an oil-in-water emulsion characterized in that a fumed silica particle group in which lower order aggregates are aggregated with each other to form a higher order aggregate by a non-chemical bond forms a network-like surrounding structure including an oil inside the network-like surrounding structure, (2) an oil-in-water emulsion, wherein the network-like surrounding structure includes a self-micelle-like aggregate in which a high density part of the hydrophilic-rich lower order aggregates is in contact with an aqueous phase and a high density part of the hydrophobic-rich lower order aggregates is in contact with other hydrophobic-rich lower order aggregates to form a space inside the self-micelle-like aggregate, (3) an oil-in-water type emulsion, wherein, in the self-micelle-like aggregate, the lower order aggregates are aggregated each other to form a network-like structure.

(4) A method for producing the oil-in-water type emulsion, characterized in comprising the steps of:

preparing a fumed silica particle group at a secondary aggregate level by mixing, in a predetermined ratio, a hydrophobic-rich silica raw material in which a surface silanol group has been subjected to a hydrophobic treatment and a hydrophilic-rich silica raw material in which a surface silanol group is remained;

producing an aqueous dispersion by adding the prepared fumed silica particle group at a secondary aggregate level to water and performing shearing with a predetermined shearing speed or more, the resulting aqueous dispersion including the fumed silica particle group in which the lower order aggregates are aggregated with each other to form the higher order aggregate by a non-chemical bond, thereby forming the network-like surrounding structure including a space inside the network-like surrounding structure; and forming an emulsion by adding an oil to the produced aqueous dispersion, the oil-in-water type emulsion including a composite particle group in which the oil is included inside the network-like surrounding structure formed by the fumed silica particle group at the secondary aggregate level, (5) a method for producing an oil-in-water emulsion, comprising a step of compounding the fumed silica particle group at the secondary aggregate level and an organic surfactant in a predetermined compounding ratio so as to adjust a shape of the network-like surrounding structure before the step of producing the aqueous dispersion, (6) a method for producing an oil-in-water emulsion, wherein the network-like surrounding structure includes a self-micelle-like aggregate in which a high density part of a hydrophilic-rich lower order aggregate is in contact with an aqueous phase and a high density part of a hydrophobic-rich lower order aggregate is in contact with other hydrophobic-rich lower order aggregates to form a space inside the self-micelle-like aggregate, (7) a method for producing an oil-in-water emulsion, wherein the step of compounding the fumed silica particle group at the secondary aggregate level and the organic surfactant includes a step of determining the predetermined compounding ratio so as to adjust a binding property of the self-micelle-like aggregate to an oil drop surrounded by the self-micelle-like aggregates, and (8) a method for producing an oil-in-water emulsion, wherein the step of preparing the fumed silica particle group at the secondary aggregate level includes a step of mixing a hydrophobic-rich silica raw material and a hydrophilic-rich silica raw material by setting a total mole number ratio represented by a total number of moles of surface hydrophilic groups of the entire fumed silica particle groups obtained from each of the fumed silica particle groups/a total number of moles of surface hydrophobic groups of the entire fumed silica particle groups obtained from each of the fumed silica particle groups to a predetermined range so as to adjust a ratio of the self-micelle-like aggregates.

That is, a method for forming a granular material or powder of the present invention is:

(9) a method for forming a granular material or a powder, characterized in that the oil is an organopolysiloxane of which average composition is represented by the general formula (1):

$$R^1_a R^2_b SiO_{(4-a-b)/2} \qquad (1),$$

[in the formula (1): $R^1$, which may be the same as or different from each other in the molecule, represents a substituted or unsubstituted, saturated or unsaturated monovalent hydrocarbon group having 1 to 25 carbon atoms, a substituted or unsubstituted aromatic group having 6 to 30 carbon atoms, a hydroxyl group, an alkoxy group having 1 to 6 carbon atoms, or a hydrogen atom; $R^2$, which may be the same as or different from each other in the molecule, represents a hydrocarbon group which is a saturated or unsaturated monovalent hydrocarbon group having 1 to 25 carbon atoms, or an aromatic group having 6 to 30 carbon atoms, and in which at least one hydrogen atom on carbons is substituted with a fluorine atom; b is a positive number which does not include 0; and a+b is 0.3 or more and less than 2.5]

the method further including a step of forming the granular material or powder having variations in a particle diameter within a predetermined range by evaporating an aqueous phase by a spray dry method using an oil-in-water type emulsion produced by the method for producing the oil-in-water type emulsion, and

(10) a method for forming a granular material or a powder, characterized in that the oil is organopolysiloxane of which average composition is represented by a general formula (1)

$$R^1_a R^2_b SiO_{(4-a-b)/2} \qquad (1),$$

[in the formula (1): $R^1$, which may be the same as or different from each other in the molecule, represents a substituted or unsubstituted, saturated or unsaturated monovalent hydrocarbon group having 1 to 25 carbon atoms, a substituted or unsubstituted aromatic group having 6 to 30 carbon atoms, a hydroxyl group, an alkoxy group having 1 to 6 carbon atoms, or a hydrogen atom; $R^2$, which may be the same as or different from each other in the molecule, represents a hydrocarbon group which is a saturated or unsaturated monovalent hydrocarbon group having 1 to 25 carbon atoms, or an aromatic group having 6 to 30 carbon atoms, and in which at least one hydrogen atom on carbons is substituted with a fluorine atom; b is a positive number which does not include 0; and a+b is 0.3 or more and less than 2.5]

the method including the steps of:

forming a composite particle group in which a fumed silica particle group is strongly bound to an outer surface of an oil drop by evaporating an aqueous phase by a spray dry method using an oil-in-water type emulsion produced by the method for producing the oil-in-water type emulsion, and in applying the composite particle group to a surface of a base material, applying the fumed silica particle group to the base material first and then applying the oil to the base material afterwards.

According to the present invention, in a stage of the aqueous dispersion, when the fumed silica particle group forms the network due to the high aggregating property of the fumed silica particle, promoting exchange and/or orientation of the silica particles, while forming the three-dimensional surrounding structure forming a space inside thereof instead of a planar structure, makes it possible to produce the oil-in-water type emulsion (the Pickering emulsion) in which the oil drop is coated with the stable and homogenous self-micelle aqueous dispersion including the fumed silica particle.

More specifically, in the oil-in-water type Pickering emulsion, a ratio of hydrophobicity and hydrophilicity of the fumed silica particle group present at the interface between the aqueous phase and the oil phase is important for the stability of the emulsion. On the other hand, for example, when the secondary aggregate is formed by the aggregation of primary aggregates of the fumed silica having a very high aggregating property, forming a network between the primary aggregates or between the secondary aggregates, in particular, forming the network-like surrounding structure including the oil inside thereof promotes optimization of a contact angle (an embedding degree) of the fumed silica particle at the interface between the aqueous phase and the oil phase.

Note that, when the dispersion of the fumed silica and water is formed, the network structure starts to be formed just by charging the fumed silica into water without applying shearing due to its high aggregating property. However, applying the shearing disassembles the formed network structure and then forms a new network structure while promoting arrangement or orientation of the primary aggregates. As a result, the hydrophobic-rich aggregates, the self-micelle-like aggregates, and the hydrophilic-rich aggregates each form the network structure, while the network structure is also formed between the hydrophobic-rich aggregates, the self-micelle-like aggregates, and the hydrophilic-rich aggregates. In particular, the self-micelle-like aggregates form the network-like surrounding structure so as to include the oil inside thereof.

According to the present invention, specifications of the composite particle in the oil-in-water type emulsion can be adjusted, thus it becomes possible to isolate the stable, homogenous, and highly reliable composite particle.

It has been known that, in the oil-in-water type Pickering emulsion including a solid particle, as compared with the oil-in-water type emulsion including a surfactant, the balance between hydrophobicity and hydrophilicity of the solid particle present at the interface between the aqueous phase and the oil phase provides an important factor for the stability of the emulsion. The present inventors have found that, particularly in a case where the solid particle is the silica particle, it is important for the stability of the emulsion to form the oil-in-water type Pickering emulsion in such a manner that when the fumed silica particle group forms the network due to the high aggregating property of the fumed silica particle, the fumed silica particle group forms the three-dimensional surrounding structure forming a space inside thereof instead of the planar structure; and the oil is added to the aqueous dispersion, as a base, in which the silica particles are dispersed in water. Based on this observation and the fact that the formation mechanism of the composite particle structure of the silica particle and the oil in the Pickering emulsion is unique due to the aggregating property of the silica particle, the present inventors have found that it is possible, by paying attention to a so-called total mole number ratio between the surface hydrophilic groups and the surface hydrophobic groups of the silica particles and variations in the total mole number ratio as parameters for evaluating not only the stability of the oil-in-water type Pickering emulsion but also the stability of the aqueous dispersion in which the silica particles are dispersed in water, to lessen limitations to the selection of the silica particles and the oil as starting raw materials, achieve both the stability and characteristics of the aqueous dispersion in accordance with applications, and adjust the composite particle structure in the emulsion in accordance with applications.

As the inorganic particle used as the raw material of the aqueous dispersion including the inorganic particle of the present invention, silica is preferably used. The silica may be of various types such as fumed silica, wet silica, and colloidal silica. However, any type of silica particle has hydrophilic silanol groups on its surface and the silanol groups can be subjected to hydrophobic treatment by an alkyl group or the like at any ratio. Thus, the molar ratio of the surface hydrophilic groups and hydrophobic groups is easily set. Further, the silica forms an aggregate structure, has high affinity with various oils, is easily shifted to the Pickering emulsion, and has excellent availability and cost performance, making silica usable for a wide range of applications. Thus, silica is preferable.

A ratio of the silica particles in the inorganic particles does not always need to be 100%, and silica particles may be partially included with inorganic particles. This is because the silica particles can play a leading role in stabilizing and homogenizing the aqueous dispersion by forming a network with inorganic particles other than the silica particles, while other inorganic particles auxiliary participate in such a role.

The most preferable silica as the raw material of the aqueous dispersion is fumed silica.

The fumed silica particles form a multidimensional aggregation structure. Thus, it is possible to control the balance between the surface hydrophilic groups and hydrophobic groups and rearrange aggregation units in accordance with the aggregate level. This allows the most effective control over the stability and homogeneity of the aqueous dispersion for implementation of the present invention.

Further, the fumed silica particle, which has a porous structure, has a large surface area and more enhanced functions in association and adsorption, making it possible to produce the more stable and homogenous aqueous dispersion. Further, the increased functions of associating and adsorbing to various oils provide an advantage in shifting to the Pickering emulsion.

The primary particle of the fumed silica particle as a minimum unit normally has a size of about 5 to 30 nanometers. The primary particles are aggregated each other to form the primary aggregate, that is, the secondary particle. The primary aggregate normally has a size of about 100 to 400 nanometers. The primary particles are fused together by a chemical bond, thus it is normally difficult to disassemble the primary aggregate. Further, the primary aggregates are aggregated with each other to form an aggregate structure, which is referred to as a secondary aggregate or a tertiary particle. The secondary aggregate has a size of about 10 An aggregate form between the primary aggregates in the secondary aggregate is not normally caused by the chemical bond, but by an associative aggregation force such as a hydrogen bond. Thus, a part or the whole of the secondary aggregate can be disassembled to the primary aggregate level by applying some external force, for example, by applying a shearing force at a predetermined level or more in water. The disassembled secondary aggregate can be reaggregated into the original secondary aggregate by removing the external force.

Note that, in the description of the present invention, the primary and secondary aggregates are also appropriately referred to as the silica particle groups at the primary and secondary aggregate levels, respectively.

For the fumed silica particle in a powder state, the secondary aggregate is usually the largest aggregation level. However, the secondary aggregates can be further aggregated with each other in the aqueous dispersion. Such an aggregate can be disassembled by a force weaker than the one used for disassembling the secondary aggregate.

However, the above-described aggregate levels such as the primary aggregate and the secondary aggregate are not always formed in a clearly distinct manner. For example, the aggregate levels at the intermediate stages between the primary aggregate and the secondary aggregate may be distributed in continuity in some degree and coexist. The primary aggregate and the secondary aggregate are defined by including such a distribution range.

It is known that the fumed silica particles, particularly at the secondary aggregate level, form a network structure. This sometimes improves usability of the fumed silica particle as the inorganic particle for the Pickering emulsion.

More specifically, as shown in FIG. 1 (note that this is just a schematic diagram, and a sectional view is shown for the sake of clarity although the network-like surrounding structure of the fumed silica particles actually coats the whole outer circumferential surface of the oil drop), the fumed silica particle group forms the network due to the high aggregating property of the fumed silica particle. The network is formed not in a planar structure, but in a three-dimensional surrounding structure forming a space inside thereof. As described below, when the aqueous dispersion including the fumed silica particle group and water is formed, the fumed silica particle group exhibiting a surfactant-like function forms the three-dimensional surrounding structure forming a space inside thereof to be present on the surface of the oil drop serving as the interface between the aqueous phase and the oil phase (the oil drop). When the oil is added to such an aqueous dispersion afterwards, the three-dimensional surrounding structure is formed so as to coat the oil drop.

Thus, as described below, it is likely that the self-micelle-like aggregate, the hydrophilic-rich aggregate, and the hydrophobic-rich aggregate can be distinguished by determining the aggregate of the fumed silica particles covering the outer circumferential surface of the single oil drop used as a base.

A state of the aqueous dispersion including the inorganic particle according to the present invention in water, a method for producing the aqueous dispersion, and an application of the aqueous dispersion, in a case of using the fumed silica as a raw material, will be described below. In the description, the terms, the primary aggregate level and the secondary aggregate level, are used to describe not only the aggregate levels including the corresponding aggregate levels by 100%, but also the aggregate levels primarily including the corresponding aggregate levels.

A basic part is in common with the aqueous dispersion including the inorganic particle which is not the fumed silica.

FIG. 2 shows what types of aggregates can be produced when the fumed silica particles are dispersed in water. In the present description, the terms, "hydrophilic-rich aggregate", "hydrophobic-rich aggregate", and "self-micelle-like aggregate" are used for the sake of convenience. The self-micelle-like aggregate is a new concept found in the present invention. Further, a description will be given of a relation between these three types of the aggregates found in the present invention.

If a molar ratio of the surface hydrophilic groups/hydrophobic groups of the fumed silica particle is hydrophilic-group rich, the silica particle surface has an affinity to water and the silica particle is easily dissolved in water. Thus, a secondary aggregate 14 is most likely stably dissolved in water as a single aggregate without further being aggregated. As a result, the aqueous dispersion has a low viscosity and a low thixotropic property. Such an aggregate is referred to as a hydrophilic-rich aggregate.

If the molar ratio of the surface hydrophilic groups/hydrophobic groups of the fumed silica particle is hydrophobic-group rich, the silica particle surface has little affinity to water and the silica particles are arranged with each other so as to minimize a contact area with water. Thus, the silica particles tend to be aggregated. In water, a large number of the secondary aggregates 14 are assembled together to form an aggregate. As a result, the aqueous dispersion has a high viscosity and a large thixotropic property. In such a state, the stability of the aqueous dispersion is not good. Precipitation of the silica particles or the like tends to occur with the lapse of time. Such an aggregate is referred to as a hydrophobic-rich aggregate. The hydrophobic fumed silica of such a state has been already used as a thickener and a thixotropic property imparting agent. However, there is a limitation that a user needs to apply the hydrophobic fumed silica to a target material immediately after the silica particles are dispersed in water.

If the molar ratio of the surface hydrophilic groups/hydrophobic groups of the fumed silica particle is in a region between the hydrophilic-rich aggregate and the hydrophobic-rich aggregate, the secondary aggregates 14 can form an aggregate in which a part of the secondary aggregate 14 having a high density of primary aggregates 10 with a relatively high hydrophilicity is in contact with an aqueous phase and a part of the secondary aggregate 14 having a high density of primary aggregates 12 with a relatively high hydrophobicity is in contact with other secondary particles. Such an aggregate has an aggregate form similar to that of a normal self-micelle including a surfactant and thus is referred to as a self-micelle-like aggregate. In this state, the aggregate number of the secondary aggregates 14 is limited to a small number and the size of the aggregate naturally becomes homogeneous, thus a stable and homogeneous aqueous dispersion is formed. An outer part of the self-micelle-like aggregate, that is, the part in contact with the aqueous phase, has a high concentration of hydrophilic groups, and thus, similar to the hydrophilic-rich aggregate, the self-micelle-like aggregate can obtain sufficiently high stability. The self-micelle-like aggregate is much more stable than the hydrophobic-rich aggregate. The self-micelle-like aggregate includes a space 16 having an oleophilic environment in its inside, thus the oil can be easily taken in from the outside. The self-micelle-like aggregate has intermediate characteristics between the hydrophilic-rich aggregate and the hydrophobic-rich aggregate in terms of viscosity and thixotropic properties. A self-micelle including a surfactant is formed when the surfactant becomes excessive in relation to the oil to be emulsified. However, the self-micelle-like aggregate including the fumed silica particles can be formed regardless of the presence of the oil and with little influence by the concentration of the fumed silica particles.

The surfactant at a low concentration sufficiently interacts with water molecules and is dissolved as a single surfactant molecule or a single surfactant ion state (a monodisperse state). However, the concentration of the monodisperse state becomes saturated at a specific concentration or higher, and the surfactants at the saturated concentration or higher start to form a supermolecule or a self-organizing body through association, which is a so-called self-micelle. The self-micelle normally has an association structure with a hydrophilic part on the outside and a hydrophobic part on the inside.

The present inventors note that, also in the aqueous dispersion state including the silica at the second aggregate level, the self-micelle-like aggregate having the association structure with the hydrophilic part on the outside and the hydrophobic part on the inside is similarly formed when the silica at the second aggregate level exceeds the saturation concentration. However, the saturation concentration is significantly lower than that of the surfactant.

These three types of aggregates are relatively defined as follows.

The hydrophobic-rich aggregate is a mass of the fumed silica particle groups having a high aggregate level, which exhibits hydrophobicity enough to exhibit a thixotropic property as compared with the self-micelle-like aggregate and the hydrophilic-rich aggregate as the aggregates of the fumed silica particles. The hydrophilic-rich aggregate is a mass of the fumed silica particle groups having a low aggregate level, which exhibits hydrophobicity enough to be soluble in water as compared with the self-micelle-like aggregate and the hydrophobic-rich aggregate as the aggregates of the fumed silica particles. The self-micelle-like aggregate is a mass of the fumed silica particle groups which exhibits hydrophobicity on the inside and hydrophilicity on the outside and has the aggregate level between the hydrophobic-rich aggregate and the hydrophilic-rich aggregate as compared with the hydrophobic-rich aggregate and the hydrophilic-rich aggregate as the aggregates of the fumed silica particles. The self-micelle-like aggregate includes an oleophilic space in its inside and thus has a structure that allows oil to be easily taken in from the outside.

Inorganic particles other than the fumed silica particles may also have such three types of the aggregate forms.

When the aqueous dispersion including the fumed silica particles is produced, regardless of the types of the aggregates to be formed, the silica particles as the raw material are hardly spontaneously dissolved or dispersed in water, and thus it is necessary to use some device which applies a shearing force. The production can be performed by using a conventional mixer, for example, a homogenizer, a colloid mill, a homomixer, and a high-speed stator-rotor stirring device.

The compounding amount of the fumed silica particles in the aqueous dispersion is preferably within a range of 0.1 to 30.0 mass %, more preferably within a range of 0.2 to 10 mass %, relative to the total amount of the aqueous dispersion composition. If the compounding amount is less than 0.1 mass %, the aggregation sometimes does not proceed, while if the compounding amount is more than 30.0 mass %, the viscosity becomes too large and exceeds a proper range of the stirring device.

The aggregation force between the primary aggregates of the fumed silica particles is released by applying a specific shearing force, and the primary aggregates are aggregated again when the shearing is removed. Thus, in the production of the aqueous dispersion, when the fumed silica particle group forms the network due to the high aggregating property of the fumed silica particles, applying the specific shearing allows the exchange of the primary aggregates between the different secondary aggregates, while the fumed silica particle group forms the three-dimensional surrounding structure forming a space inside thereof instead of a planar structure. This makes it possible to change a ratio between the hydrophilic-rich primary aggregates and the hydrophobic-rich primary aggregates in the single secondary aggregate. Such an exchange of the primary aggregates between the secondary aggregates is referred to as rearrangement.

The rearrangement is caused preferably by applying shearing at a speed of 7,500 $s^{-1}$ or more. The shearing speed less than 7,500 $s^{-1}$ does not cause the sufficient rearrangement. The upper limit value of the shearing speed for causing the rearrangement is not limited; however, if the shearing speed is more than 100,000 $s^{-1}$, for example, the following problems may arise: a malfunction of the device tends to occur, a water content of the aqueous dispersion is evaporated by heating, and the oil, if present, is decomposed. Thus, it is not preferable.

Causing the sufficient rearrangement promotes the exchange of the primary aggregates between the secondary aggregates. As a result, the ratio between the hydrophilic-rich primary aggregates and the hydrophobic-rich primary aggregates in the secondary aggregate of the fumed silica particles becomes more homogenous in the entire aqueous dispersion system.

Further, when the fumed silica particle group forms a network due to the high aggregating property of the fumed silica particles, applying the shearing speed enough for causing the rearrangement to the aggregate of the silica particles may cause a movement and a change in arrangement of the primary aggregates in the same secondary aggregate, while the fumed silica particle group forms the three-dimensional surrounding structure forming a space inside thereof instead of a planar structure. Further, when the self-micelle-like aggregate is formed, as shown in FIG. 2, the hydrophobic primary aggregates may be oriented toward an aggregation direction of two particles.

As described above and schematically shown in FIG. 2, the types of the most easily formed aggregates change depending on a degree of hydrophilicity/hydrophobicity of the fumed silica particles.

More specifically, if the total mole number ratio represented by the total number of moles of the surface hydrophilic groups of the entire fumed silica particle groups obtained from each of the fumed silica particle groups/the total number of moles of the surface hydrophobic groups of the entire fumed silica particle groups obtained from each of the fumed silica particle groups is a predetermined lower limit or less, the hydrophobic-rich aggregates are primarily produced. Further, if the total molar ratio is a predetermined upper limit or more, the hydrophilic-rich aggregates are primarily produced. Further, if the total molar ratio is the predetermined lower limit or more and the predetermined upper limit or less, the self-micelle-like aggregates are primarily produced.

In case of the fumed silica, the lower limit value of the total molar ratio is about 20/80. The upper limit value is about 80/20.

In the present invention, it was unexpectedly found that applying a certain level or more of shearing force causes the rearrangement of the fumed silica particles without being restricted by the state of the fumed silica as a starting material. That is, in a stage of a raw material, the total mole number ratio represented by the total number of moles of the surface hydrophilic groups of the entire fumed silica particle groups obtained from each of the fumed silica particle groups/the total number of moles of the surface hydrophobic groups of the entire fumed silica particle groups obtained from each of the fumed silica particle groups is only required to be set to 20/80 or more and/or 80/20 or less for any types of the silica as a raw material. The hydrophilic silica particle in which a surface silanol group is remained, the hydrophobic silica particle having a surface silanol group having been subjected to the hydrophobic treatment, or a mixture thereof at any ratio may be used. Further, the fumed silica having been subjected to the hydrophobic treatment at any ratio may be used. Commercially available fumed silica particles can be used. Alternatively, the hydrophilic silica particle can be hydrophobized by a known method of treating the hydrophilic silica particle with halogenated organic silicon such as methyltrichlorosilane, alkoxysilanes such as dimethyldialkoxysilane, silazane, and low molecular weight methylpolysiloxane.

The specific surface area under a dry condition of the silica particle described above is preferably 2 to 350 $m^2/g$ in a fine powder state, more preferably 50 to 300 $m^2/g$.

As a raw material, the above-described types of fumed silica particles can be used; however, in the stage of a raw material, the total mole number ratio represented by the total number of moles of the surface hydrophilic groups of the entire fumed silica particle groups obtained from each of the fumed silica particle groups/the total number of moles of the surface hydrophobic groups of the entire fumed silica particle groups obtained from each of the fumed silica particle groups needs to be set to 20/80 or more and/or 80/20 or less.

In this case, when the aqueous dispersion including water and the fumed silica particle group is formed, the network structure is formed by the fumed silica particles due to the high aggregating property of the fumed silica particles by filling the water with the fumed silica particle group before applying a certain level or more of the shearing force. This network structure is primarily formed between the secondary aggregates, and a part or the whole of the secondary aggregates can be disassembled to the primary aggregates by applying some external force such as the shearing. The network structure is disassembled by applying a certain level or more of the shearing force. Then, as described above, while the three-dimensional network-like surrounding structure forming a space inside thereof is formed again at the primary aggregate level, the exchange at the primary aggregate level between the fumed silica particle groups at the secondary aggregate level and/or the orientation at the primary aggregate level in the fumed silica particles at the secondary aggregate level are promoted on the basis of the aggregating property of the fumed silica particles. In this manner, the self-micelle-like aggregate having a high density of hydrophilic parts on the outside and a high density of hydrophobic parts on the inside can be primarily formed, and the homogenization of the primarily formed self-micelle-like aggregates can be promoted.

The aqueous dispersion including the inorganic particles obtained by the present invention is stable and homogenous and has a function of imparting viscosity and thixotropic properties. Such an aqueous dispersion has not been available up to now, thus a very large number of new applications can be developed. Further, the aqueous dispersion of the present invention can be produced by adjusting the molar ratio of the hydrophilic groups and the hydrophobic groups in the stage of a raw material using a commercially available silica and a conventional device, thereby offering great advantages in costs and processes.

According to the present invention, the existence ratio of the hydrophobic-rich aggregates, the hydrophilic-rich aggregates, or the self-micelle-like aggregates can be changed by setting the total molar ratio of the fumed silica particles. This allows development of new applications.

The self-micelle-like aggregate has functions of imparting a thickening effect and thixotropic properties, though not so much as the hydrophobic-rich aggregate. Further, the self-micelle-like aggregate is excellent in stability and homogeneity.

Thus, setting the total molar ratio to 20/80 or more causes a state in which the self-micelle-like aggregates and the hydrophobic-rich aggregates coexist. In such a case, the stability is increased compared with a thickener and a thixotropic property imparting agent using the conventional hydrophobic silica. That is, new applications with the emphasis on both the stability and the viscosity/the thixotropic property can be developed. For example, when the aqueous dispersion is used in a coating material and a polymer material for imparting the viscosity and the thixotropic property, instability which causes precipitation of the silica properties conventionally found is not exhibited, thus commercial production can be possible as a stable aqueous dispersion.

A user does not need to prepare the aqueous dispersion due to increased storage stability for the user, thus handleability is increased.

Setting the total molar ratio to 80/20 or less causes a state in which the self-micelle-like aggregates and the hydrophilic-rich aggregates coexist. In such a case, the viscosity and the thixotropic property are increased to some extent as compared with a conventional hydrophilic fumed silica, which is stable, but hardly provides the increased viscosity and thixotropic property. That is, new applications with the emphasis on both the stability and the low viscosity can be developed. For example, new applications can be developed for cream, an emulsified cosmetic, or the like, where the low viscosity and thixotropic property, and the excellent stability are both required. Further, a user does not need to prepare the aqueous dispersion due to the excellent storage stability at the user side, and thus handleability is increased.

Setting the total molar ratio to 20/80 or more and 80/20 or less causes a state in which the self-micelle-like aggregates predominantly exist. This state is stable and exhibits certain levels of the viscosity and the thixotropic property. Further, this state is homogenous without including the hydrophobic-rich aggregates and the hydrophilic-rich aggregates.

Thus, it becomes possible to provide a stable and homogenous function-imparting agent mainly focusing on the viscosity and the thixotropic property, allowing development of a very large number of applications. Variations in functions in the same batch and variations between batches can also be reduced. As applications that can take advantage of such characteristics, a very large number of applications, such as a cosmetic, a functional coating material, a functional coating agent, an adhesive, and a sealant for construction, may be mentioned. Further, the desirable levels of the viscosity and the thixotropic property can be imparted in each application by appropriately adjusting the total molar ratio. Further, a user does not need to prepare the aqueous dispersion due to the excellent storage stability at the user side, thus handleability is increased.

The Pickering emulsion according to the present invention is the oil-in-water type emulsion, which includes the composite particle groups including the self-micelle-like aggregates formed by the fumed silica particle groups as the secondary aggregate and the oil inside the self-micelle-like aggregates, in each composite particle group, the surface of the oil drop being coated with the self-micelle-like aggregates. The self-micelle-like aggregates are stable in the aqueous dispersion and this state is essentially preserved in the Pickering emulsion.

The stable, homogenous, and highly reproducible Pickering emulsion can be produced by coating the oil drop with the self-micelle-like aggregates.

The secondary aggregate of the fumed silica exists reportedly in a size of about 10 μm in a normal condition. However, in the oil-in-water type emulsion according to the present invention, the aggregated matters of the spherical silica particles are used for coating and each aggregated matter normally has a size of about 0.1 μm to several μm. Thus, a small portion of the secondary aggregates includes the primary aggregates and may possibly include the intermediate aggregates at the stage of shifting from the primary aggregates to the secondary aggregates. Alternatively, it is also conceivable that the secondary aggregates are more densely formed than the secondary particles existing in a usual state.

The oil contained in the oil-in-water type emulsion composition of the present invention is not limited, and any kind of oil component may be used. For example, silicone, mineral oil, synthetic oil, vegetable oil, animal oil, and the like can be used.

Silicone is a preferred oil since it provides excellent properties in a wide range of industrial and cosmetic applications. The type is not limited. Examples thereof may include linear polysiloxanes (such as dimethylpolysiloxane, methylphenylpolysiloxane, and diphenylpolysiloxane), cyclic polysiloxanes (such as octamethylcyclotetrasiloxane, decamethylcyclopentasiloxane, and dodecamethylcyclohexasiloxane), silicone resins which form a three-dimensional network structure, silicone rubber, various modified polysiloxanes (such as amino-modified polysiloxane, polyether-modified polysiloxane, alkyl-modified polysiloxane, and fluorine-modified polysiloxane), alkenyl-modified polysiloxanes, hydrogen polysiloxane, and acrylic silicones.

The viscosity of the oil is also not limited. Also, as long as it is fluid, the oil may contain solid components. In addition, the oil may be a flowable rubber or rubber-containing material, or a curable rubber composition which is cured after formation of an emulsion to form a rubber.

When the oil contained in the oil-in-water type emulsion composition is a fluorine-containing organopolysiloxane, the average composition formula thereof is represented by the general formula (1):

$$R^1_a R^2_b SiO_{(4-a-b)/2} \qquad (1)$$

In the formula (1): $R^1$, which may be the same as or different from each other in the molecule, represents a substituted or unsubstituted, saturated or unsaturated monovalent hydrocarbon group having 1 to 25 carbon atoms, a substituted or unsubstituted aromatic group having 6 to 30 carbon atoms, a hydroxyl group, an alkoxy group having 1 to 6 carbon atoms, or a hydrogen atom; $R^2$, which may be the same as or different from each other in the molecule, represents a hydrocarbon group which is a saturated or unsaturated monovalent hydrocarbon group having 1 to 25 carbon atoms, or an aromatic group having 6 to 30 carbon atoms, and in which at least one hydrogen atom on carbons is substituted with a fluorine atom; b is a positive number which does not include 0; and a+b is 0.3 or more and less than 2.5

'a' and 'b' herein are numerical values related to the order of the siloxane bond, and when a+b is 2.0, the component (A) represents a linear siloxane. In the present invention, since a+b is 0.3 or more and less than 2.5, the component (A) may be any form of oil, rubber, resin, curable composition and the like.

Specific examples of the above-described organic group $R^1$ may include alkyl groups such as a methyl group, an ethyl group, a propyl group, an isopropyl group, a butyl group, an isobutyl group, a t-butyl group, a pentyl group, a neopentyl group, a hexyl group, a 2-ethylhexyl group, a heptyl group, an octyl group, a nonyl group, a decyl group, and a dodecyl group; cycloalkyl groups such as a cyclopentyl group, a cyclohexyl group, and a cycloheptyl group; aryl groups such as a phenyl group, a tolyl group, a xylyl group, a biphenyl group, and a naphthyl group; aralkyl groups such as a benzyl group, a phenylethyl group, a phenylpropyl group, and a methylbenzyl group; nitrogen-containing hydrocarbon groups represented by —$CH_2$—$CH_2$—$CH_2$—$N_2$, —$CH_2$—$CH_2$—$CH_2$—$NH(CH_3)$, —$CH_2$—$CH_2$—$CH_2$—$N(CH_3)_2$, —$CH_2$—$CH_2$—$NH$—$CH_2$—$CH_2$—$NH_2$, —$CH_2$—$CH_2$—$CH_2$—$NH(CH_3)$, —$CH_2$—$CH_2$—$CH_2$—$NH$—$CH_2$—$CH_2$—$NH_2$, —$CH_2$—$CH_2$—$CH_2$—$NH$—$CH_2$—$CH_2$—$N(CH_3)_2$, —$CH_2$—$CH_2$—$CH_2$—$NH$—$CH_2$—$CH_2$—$NH(CH_2CH_3)$, —$CH_2$—$CH_2$—$CH_2$—$NH$—$CH_2$—$CH_2$—$N(CH_2CH_3)_2$, and —$CH_2$—$CH_2$—$CH_2$—$NH$—$CH_2$—$CH_2$—$NH(cyclo$-$C_6H_{11})$; and substituted hydrocarbon groups in which part or all of hydrogen atoms in the hydrocarbon group are substituted by a halogen atom, cyano group or the like such as a chloromethyl group, a 2-bromoethyl group, a 3,3,3-trifluoropropyl group, a 3-chloropropyl group, a chlorophenyl group, a dibromophenyl group, a tetrachlorophenyl group, a difluorophenyl group, a β-cyanoethyl group, a γ-cyanopropyl group, and a β-cyanopropyl group.

Particularly preferred organic groups are the methyl group and the phenyl group.

In addition, a substituent that causes a curing reaction, for example, an unsaturated hydrocarbon group such as a vinyl group or an allyl group, hydrogen bonded to a silicon atom, or the like may be included.

The above-described organic group $R^2$ is a saturated or unsaturated monovalent hydrocarbon group having 1 to 25 carbon atoms, or an aromatic group having 6 to 30 carbon atoms, and specifically, is an organic group in which a hydrogen atom on at least one carbon atom of the saturated or unsaturated monovalent hydrocarbon group or aromatic group exemplified as the $R^1$ is substituted by a fluorine atom.

In the fluorine-containing organopolysiloxane, the number of moles a of the organic group $R^1$ per mole of the silicon atom and the number of moles b of the organic group $R^2$ per mole of the silicon atoms are not particularly limited as long as b is a positive number other than 0 and a+b is 0.3 or more and less than 2.5.

It is preferable that a+b is 0.8 or more and less than 2.2. If the value is less than 0.8, the proportion of the tetrafunctional resin increases, making it difficult to produce an emulsion because it is solid. If the value is 2.2 or more, the silane component is increased in amount, the volatility becomes high and it is difficult to apply it to various applications.

The ratio of the organic group $R^1$ and the organic group $R^2$, that is, a/b is not particularly limited, but is preferably 5/95 or more and less than 95/5. If it is less than 5/95, the properties as a typical organopolysiloxane, such as flexibility, is not sufficient, and if it is 95/5 or more, the content of the organic group containing fluorine is small, so that the characteristics derived from fluorine cannot be sufficiently exerted.

The fluorine-containing organopolysiloxane is not limited in its chemical structure, molecular weight, or properties, as long as the above-described conditions are satisfied. Moreover, the form may be any form such as liquid, solid, flake, powder and the like.

The fluorine-containing organopolysiloxane may be either a single component or a mixture of two or more components.

It is preferable that neither the organic group $R^1$ nor the organic group $R^2$ contain a hydrophilic substituent, for example, a hydroxyl group, a carboxyl group, an amino group, or an alkoxy group. If it is used for an intended use application, the water repellency and water resistance inherent in fluorine-containing organopolysiloxanes are sacrificed.

In each composite particle present in the oil-in-water type emulsion according to the present invention, the oil drop is coated with the self-micelle-like aggregates including the fumed silica particles. In this state, the coating may be formed by a single layer of the secondary aggregates or multiple layers of the secondary aggregates. Further, alternatively, there may be a part in which the oil drop is not coated with the fumed silica particles.

A part of the secondary aggregate in contact with the oil drop is embedded into the oil drop. The embedding degree varies depending on a degree of polarity of the oil and the molar ratio between the surface hydrophilic groups and hydrophobic groups of the fumed silica secondary aggregate. If the polarities of the oil drop and the secondary aggregate are similar to each other, for example, if the oil drop is formed by a silicone and the polarities of the surface of the secondary particle and the silicone are similar to each other, the embedding degree is increased due to high affinity. Conversely, the embedding degree is reduced if the difference in polarities is large.

It is believed that obtaining a contact angle determined by three factors, the inorganic particle, the oil drop, and water, as an optimal value is important for allowing the Pickering emulsion to stably exist. In the oil-in-water type emulsion according to the present invention, the embedding degree of the secondary aggregate including the fumed silica particles into the oil drop is primarily determined by the above-described mechanism. However, it is possible that, in the process of completing the emulsion, when the fumed silica particle group forms the network due to the high aggregating property of the fumed silica particles, applying an appropriate shearing force induces the movement of the primary aggregates in the secondary aggregate and the orientation of the primary aggregates having high hydrophobicity along the direction of the oil drop to create a gradient distribution of polarities inside the secondary particle, while the fumed silica particle group forms the three-dimensional surrounding structure forming a space inside thereof instead of a planar structure. It is possible that the optimal contact angle that causes the emulsion to exist in the most stable manner is obtained by determining the embedding degree through a self-adjustment of the aforementioned gradient distribution.

Further, the secondary aggregate can be moved by applying an appropriate shearing force after the emulsion is formed. The secondary aggregate can be moved on the surface of the oil drop to uniformize their intervals and homogenize a state of the layer. Further, a part of the secondary aggregates can be moved between the composite particles.

The coating of the oil drop with the secondary aggregates of the fumed silica particles includes a partial coating in addition to the entire coating. As an index for representing a coating degree, the thickness of the silica layer and a result of morphological observation may be conceived. In this time, the use of a coating amount as the more practical coating degree enables the control of properties. The properties herein refer to the properties of the emulsion (the stability, etc.) and, in a case where the composite particles are isolated to be used, the properties of the isolated composite particles, such as an anti-blocking property.

The amount of the coating layer including the silica particles on the surface can be parameterized as a weight of the fumed silica particles per unit area of the surface of the oil drop.

In the present invention, this amount of the silica coating layer can be controlled by a processing amount of the silica particles relative to the surface area calculated from the particle diameter of the composite particle. This amount is preferably in a range of $2.0 \times 10^{-9}$ to $3.2 \times 10^{-6}$ kg/m$^2$. If the amount is less than $2.0 \times 10^{-9}$ kg/m$^2$, blocking is caused to the composite particle in water or after isolated. If the amount exceeds $3.2 \times 10^{-6}$ kg/m$^2$, an unfavorable phenomenon in a specific application, for example, the sense of coarseness in a cosmetic, is caused due to the increased friction of the composite particle and the like, and contamination with excessive silica in the emulsion or after the isolation of the particles or the like also occurs.

The particle diameter of each composite particle present in the oil-in-water type emulsion according to the present invention is affected by a mass ratio of the fumed silica particles relative to the total amount of the oil. The particle diameter decreases as the ratio increases. However, the particle diameter is maintained to about 10 μm regardless of the types of the oil as long as the amount of the silica coating layer is within the above-described preferable range. This particle diameter is larger than the particle diameter of the particle of the emulsion emulsified by a conventional organic surfactant; however, the composite particle having such a particle diameter are stable and homogenous. In various applications, the particle diameter of about 100 μm or less is preferable as the Pickering emulsion. If the particle diameter is more than 100μ, the stability of the emulsion decreases and, in a case where the composite particles are isolated and used, for example, in a cosmetic application, the size of powder becomes large enough to be sensed by touching, thus such a particle diameter is not preferable from the viewpoint of use feeling.

Variations in the particle diameter of the composite particle group present in the oil-in-water type emulsion according to the present invention are small. This is because the surface of the oil drop is coated with the self-micelle-like aggregates including the fumed silica particles. The self-micelle-like aggregates in the aqueous dispersion are homogenous and thus cause homogenous effects on the oil drop, thus variations in the particle diameter become small.

Further, a step of compounding the fumed silica particle group at the secondary aggregate level and the organic surfactant in a predetermined compounding ratio so as to adjust a shape of the network-like surrounding structure may be included. The step of compounding the fumed silica particle group at the secondary aggregate level and the organic surfactant may include a step of determining a predetermined compounding ratio so as to adjust a binding property of the self-micelle-like aggregates to the oil drop surrounded by the self-micelle-like aggregates.

More specifically, the fumed silica particle group at the secondary aggregate level and the organic surfactant are both present on the outer surface of the oil drop constituting the interface between the aqueous phase and the oil phase, and the contact angle (the embedding degree) of the fumed silica particle group at the secondary aggregate level and the organic surfactant to the oil drop is determined by a relationship of three factors, the aqueous phase, the oil phase, and the fumed silica particle group at the secondary aggregate level and the organic surfactant. That is especially why, when the fumed silica particle group at the secondary aggregate level and the organic surfactant are compounded, as compared with a case where only the fumed silica particle group at the secondary aggregate level is present on the interface without the organic surfactant, the size of the inner space constituted by the network-like surrounding structure and the contact angle (the embedding degree) of the fumed silica particle group at the secondary aggregate level to the oil drop are affected in accordance with the compounding ratio. This makes it possible, through trial and error, to adjust the specifications of the composite particle including the self-micelle-like aggregates and the oil, such as, for example, the size and shape of the composite particle and the binding property of the fumed silica particle group at the secondary aggregate level to the oil drop.

In this case, the mass ratio of the fumed silica particles relative to the total amount of the oil and the compounding ratio of the fumed silica particle group at the secondary aggregate level and the organic surfactant may be combined.

The oil-in-water type emulsion according to the present invention can be produced by using the stirring device similar to the device used for producing the aqueous dispersion including the fumed silica particles.

For coating the surface of the oil with the self-micelle-like aggregates including the fumed silica particles, as an order of processing, it is necessary that the self-micelle-like aggregates including the fumed silica particles are first formed and then the oil is charged afterwards. This is because, if the oil is first charged, the self-micelle-like aggregates including the fumed silica particles are not formed and thus the oil-in-water type emulsion, an intended Pickering emulsion, cannot be produced.

Thus, in a first step of the production method, the fumed silica particle group at the secondary aggregate level is prepared so as to have the total mole number ratio represented by the total number of moles of the surface hydrophilic groups of the entire fumed silica particle groups obtained from each of the fumed silica particle groups/the total number of moles of the surface hydrophobic groups of the entire fumed silica particle groups obtained from each of the fumed silica particle groups of 20/80 or more and 80/20 or less. In order to confine the total molar ratio within the predetermined value range, the molar ratio of the fumed silica as a raw material is adjusted as performed in the method for producing the self-micelle-like aggregates in the aqueous dispersion.

Next, in the second step, the prepared fumed silica particle group at the secondary aggregate level is added to water. When the fumed silica particle group forms the network due to the high aggregating property of the fumed silica particles, applying the shearing at a predetermined shearing speed promotes the exchange at the primary aggregate level between the fumed silica particle groups at the secondary aggregate level and/or the orientation at the primary aggregate level in the fumed silica particles at the secondary aggregate level, while the fumed silica particle group forms the three-dimensional surrounding structure forming a space inside thereof instead of a planar structure, to produce the aqueous dispersion including the self-micelle-like aggregates formed by the fumed silica particle group at the secondary aggregate level such that a difference between the average value of the total mole number ratio and the molar ratio represented by the number of moles of the surface hydrophilic groups/the number of moles of the surface hydrophobic groups in each of the secondary particles constituting the fumed silica particle group becomes a predetermined value or less. The rearrangement is preferably caused by applying the shearing at a speed of 7,500 s$^{-1}$ or more.

Next, in the third step, the oil is added to the aqueous dispersion thus produced to form the emulsion. This process is performed by using the stirring device and applying the appropriate shearing speed and requires time for appropriately performing the shearing to uniformly form a structure as the composite particle in which the surface of the oil drop is uniformly coated with the self-micelle-like aggregates. The shearing speed does not need to be 7,500 s$^{-1}$ or more as is required for the rearrangement, and about several thousand per second of the shearing speed is normally sufficient.

It is important to primarily produce the self-micelle-like aggregates by setting the total mole number ratio represented by the total number of moles of the surface hydrophilic groups of the entire fumed silica particle groups obtained from each of the fumed silica particle groups/the total number of moles of the surface hydrophobic groups of the entire fumed silica particle groups obtained from each of the fumed silica particle groups within the predetermined value range for producing the stable and homogenous Pickering emulsion. It is preferable to minimize variations in the state of the self-micelle-like aggregates in each composite particle in which the surface of the oil drop is coated with the self-micelle-like aggregates (e.g., the embedding degree of the secondary aggregates into the oil drop at the interface). As the variations become smaller, the self-micelle-like aggregates are more strongly associated with each other, thus the composite particle tends to become more stable. Then, this stabilizes the entire composite particle groups and reduces variations in the state of each composite particle.

Variations between the secondary aggregates can be reduced in the second step of the above-described production method. When variations in the degree of hydrophobicity (the degree of hydrophilicity) in each secondary aggregate are small, variations in the embedding degree of the secondary aggregates in contact with the oil drop in each self-micelle-like aggregate also become small. When the variations in the degree of hydrophobicity (the degree of hydrophilicity) in each second aggregate are approximately in a range of about −60% to +60% of the average value of the variations in the degree of hydrophobicity (the degree of hydrophilicity) in the entire secondary aggregates, the stable oil-in-water type emulsion can be formed.

Reduction of the variations between the secondary aggregates can be achieved not only by causing the rearrangement by applying the shearing but also by using the fumed silica particles in which the hydrophilic groups are hydrophobized at a specific hydrophobic ratio as a raw material. However, such a method requires high production costs. Without using such special silica particles, the production can be achieved with a simple method simply by using commercially available inexpensive hydrophilic fumed silica particles and hydrophobic fumed silica particles as raw materials and adjusting the mass ratio so as to obtain the predetermined total molar ratio.

The variations in the state of the composite particles can be reduced by promoting the orientation at the primary aggregate level in the fumed silica particles at the secondary aggregate level without significantly reducing the variations in the degree of hydrophobicity (the degree of hydrophilicity) of the secondary aggregates. This is because, as the orientation is enhanced, the concentration of the hydrophobic groups near the parts where the secondary aggregates are in contact with the oil drop interface increases, while the concentration of the hydrophilic groups near the parts where the secondary aggregates are in contact with the aqueous phase increases, thus the embedding into the oil drop and the affinity to the aqueous phase are both efficiently improved.

When the variations in the degree of hydrophobicity (the degree of hydrophilicity) of the secondary aggregates is reduced and the orientation at the primary aggregate level in the fumed silica particles at the secondary aggregate level is enhanced, the synergistic effect can be exhibited to produce the more stable and homogenous composite particle.

Setting of the mass ratio of the fumed silica particles and the oil is also important regarding the variations between the composite particles. As described above, it is preferable to minimize the variations in the coating layer thickness of the silica particles on the surface of the oil drop between the composite particles. For this purpose, it is preferable to set the mass of the silica particles relative to the mass of the oil within the above-described range of the coating amount for the stability.

In the oil-in-water type emulsion or the isolated composite particle of the present invention, if the silica is used as a functional particle, the mass ratio of the oil relative to the silica particles has an important meaning.

The oil-in-water type emulsion (the Pickering emulsion) in which the oil drop is coated with the fumed silica particles obtained by the present invention essentially becomes stable and homogenous in the step of producing the aqueous dispersion. Then, the auxiliary stabilization process is further performed to greatly improve the stability and homogeneity. Further, it is excellent in reproducibility and reliability and has no restrictions on the selection and form of the oil, thus allowing the development of a very large number of applications.

According to the present invention, the homogeneity of the composite particles in the aqueous dispersion can be examined by a simple method in a stage of the intermediate of the oil-in-water type emulsion, which can ensure the stability and homogeneity of the emulsion as the final product. The manufacturing yield is significantly improved without causing a defective product. Further, it is possible to perform design for this purpose.

It is expected that the emulsion as a target object can be used to improve a very large number of existing applications and develop new applications. For example, the emulsion is compounded into various cosmetics to provide various effects by attaching various silicones as the oil to the hair and skin, the emulsion is used as coating films of various electronic materials and an air bag, in which very precise and reproducible coating are required, and the emulsion is also used in coating required to be heat-resistant and homogenous such as a releasing agent for die casting.

According to the present invention, the stable and homogenous oil-in-water type emulsion can be produced and the coating layer degree of the silica layer can be controlled, and thus the reliable composite particle can be isolated and obtained.

In a case where the composite particle is isolated by removing water, if the silica functions as a functional particle in an application for a conventional reinforcing material for plastics, the composite particle is, for example, expected to provide a function of reducing hygroscopicity by the action of the oil and impart a rubber elasticity. If silicone rubber in which the oil is hardened is used, the composite particle having a soft interior and a hard surface is expected to be used as a cosmetic powder or the like that provides smooth feeling and has excellent stretchability. In these applications, the composite particles having little variations can improve the functions in the application. In a case where the silica is not a functional particle, the silicone rubber particle having the excellent homogeneity in the particle diameter and the shape can improve performance of various coating materials and plastics in which the composite particles are compounded. Further, the composite particle is considered as a new product form as a type of dry emulsions by appropriately dispersing the composite particles in water again for emulsification.

The fluorine-containing organopolysiloxane emulsion according to the present invention can be formed in a granular shape or a powder shape using various granulation or powderization methods. The form of the fluorine-containing organopolysiloxane is not limited, however, a rubber form or resin form, that is, a solid form at the normal temperature is preferable. The fluorine-containing organopolysiloxane in the rubber form is preferably prepared as a curable composition of addition reaction type or the like and cured after formation of the emulsion.

The spray dry method is preferable as the granulation or powderization method.

The fluorine-containing organopolysiloxane emulsion composition according to the present invention can be formed in the granular shape or the powder shape, and thus, as compared with a method of crushing from the rubber or resin form, the granular material or the powder has a more regular shape and less variations in size. The characteristics essentially included in the fluorine-containing organopolysiloxane, such as a small surface tension, a small intermolecular force, a high heat resistance, a high insulation, and a high dielectric constant, are synergized with the state of the granular shape or the powder shape to make it possible to impart, to a base material, performance such as water repellency, oil repellency, heat resistance, cosmetic performance, an antifouling property, weather resistance, a releasing property, long term stability, insulation, or a high dielectric constant.

In particular, a certain level of the interface tension acts on the silicone rubber particle surface layer coated with the fumed silica particles due to the network-like surrounding structure formed by the fumed silica particles or the aggregation force acting between an oil component of the silicone rubber particle before curing and the fumed silica particle, resulting in a force that acts to minimize the surface area of the dispersed oil phase. As a result, the shape of the emulsified silicone rubber particle becomes closer to a true sphere.

For obtaining the silicone rubber particle having a shape closer to a true sphere, the rate of the curing reaction should not be excessively high. That is, if the curing reaction proceeds while the oil layer having been distorted by the shearing force during the emulsification and dispersion is returning to a spherical shape by the interfacial tension on the surface layer, an intended truly spherical property is unlikely to be obtained.

A product in the granular or powder shape can be provided for various applications and handling in the various applications is safe and simple. If the product in the granular or powder shape is compounded in various plastics and the like, the above-described excellent properties can be imparted to the plastics and the like. Further, if the product in the granular or powder shape is compounded in various protective coating agents and cosmetics, the exact same effects as observed in the formation of the coating film can be imparted to base materials.

Further, properties unique to the product in the granular or powder shape, for example, enhancement of strength, smooth feeling, and the like can be imparted to various base materials.

In particular, in the cosmetic applications, in contrast with a case where the fluorine-containing organopolysiloxane in the granular or powder shape and the fumed silica in the granular or powder shape are separately applied to the hair, the skin, or the like, application of the fluorine-containing organopolysiloxane emulsion composition, which can be produced in the granular or powder shape and in which the fumed silica particle group is strongly bound to the outer surface of the oil drop, can surely create a situation where the fumed silica particle group is applied first and then the fluorine-containing organopolysiloxane as the oil drop is applied afterwards.

Next, the present invention will be described by way of examples. Note that the present invention is not limited by the examples. Further, the contents of the fumed silica used in Examples are as follows and the evaluation methods of the oil-in-water type emulsions including the fumed silica particles of the present invention and the compositions in Comparative Examples are performed as follows.

<Contents of Fumed Silica>

The silicas used in Examples and those in Comparative Examples of the present invention are silicas 1 to 3 shown in Table 1 and all of them are fumed silica (dry silica). The contents of the silica are shown in Table 1.

TABLE 1

| | Hydrophilic Dry Silica ("Silica 1") | Hydrophobic Dry Silica ("Silica 2") | Hydrophobicized Hydrophilic Dry Silica ("Silica 3") |
|---|---|---|---|
| <Contents Of Silica> | | | |
| Bet Surface Area | 200 ± 300 | 120 ± 40 | 200 ± 30 |
| Molar Ratio Of Surface Hydrophilic Groups And Surface Hydrophobic Groups In Entire Particles At Raw Material Stage | 90/10 | 10/90 | 70/30 |

<Measuring Method of Particle Diameter>

The particle diameter of the oil-in-water type emulsion particles obtained in Examples and Comparative Examples was measured by using a laser diffraction scattering particle size distribution analyzer (product name "LS-230") manufactured by Beckman-Coulter, Inc. and represented as an average particle diameter.

<Evaluation Method of Stability and Homogeneity>

An evaluation method of the stability of the oil-in-water type emulsions obtained in Examples and Comparative Examples was performed as follows: thirty grams of each sample was placed in a 50 ml screw vial and the presence of sedimentation was examined after the sample was stored for one month at the room temperature. For the emulsions, the presence of creaming was also examined. Further, the homogeneity was visually examined for the presence of a large granular material and turbidity at a peripheral part.

Evaluation Standard;

AA: homogenous with no creaming or sedimentation at all, A: less homogeneous with limited creaming and sedimentation, B: slightly inhomogeneous with moderate creaming and sedimentation, C: inhomogeneous with creaming and sedimentation <Evaluation Method of Water Repellency>

The oil-in-water type emulsions obtained in Examples and Comparative Examples were diluted to twice with water and applied on a glass plate using a bar coater to form a coating film having a thickness of about 30 μm. After sufficiently drying the coated film, a contact angle with water was measured to evaluate water repellency. The contact angle of 90 degrees or more is considered excellent in water repellency.

<Method for Producing Aqueous Dispersion and Oil-in-Water Type Emulsion in Examples and Comparative Examples>

In each of Examples and Comparative Examples, an aqueous dispersion was obtained based on preparation amounts and production conditions shown in Table 2. Further, an oil-in-water type emulsion was produced based on the preparation amounts shown in the same table with the use of the resulting aqueous dispersion.

Evaluation results of the oil-in-water type emulsions were shown in Table 3.

Example 1

As a first step, 2.5 g of hydrophilic fumed silica ("silica 1") and 2.5 g of hydrophobic fumed silica ("silica 2") were charged in a 500 mL stainless steel beaker. To this, 45 g of deionized water was charged and the mixture was stirred at 3,000 rpm for 2 minutes by using an Ultraturraxm mixer to obtain a silica aqueous dispersion. The shearing speed in this stirring was about 11,000 s$^{-1}$.

Next, as a second step, 50 g of fluorine-containing organopolysiloxane having a viscosity of 1,000 mPa·s (available under the name of AF98/1000 from Wacker Chemie AG (Munich, Germany)) was charged, and the mixture was stirred at 1,500 rpm for 2 minutes to obtain an oil-in-water type emulsion having a low viscosity and white color. The shearing speed in this stirring was about 4,600 s$^{-1}$.

Example 2

An aqueous dispersion and an oil-in-water type emulsion having a low viscosity and white color were obtained in the same manner as in Example 1 except that 1 g of the silica 1 and 4 g of the silica 2 were charged.

Example 3

An aqueous dispersion and an oil-in-water type emulsion having a low viscosity and white color were obtained in the same manner as in Example 1 except that 4 g of the silica 1 and 1 g of the silica 2 were charged.

Example 4

Five grams of partially hydrophobized hydrophilic fumed silica ("silica 3") was charged in a 500 mL stainless steel beaker. To this, 45 g of deionized water was charged and the mixture was stirred at 3,000 rpm for 2 minutes by using an Ultraturrax™ mixer to obtain a silica aqueous dispersion.

Next, 50 g of fluorine-containing organopolysiloxane having a viscosity of 1,000 mPa·s (available under the name of AF98/1000 from Wacker Chemie AG (Munich, Germany)) was charged, and the mixture was stirred at 1,500 rpm for 2 minutes to obtain an oil-in-water type emulsion having a low viscosity and white color.

Example 5

An aqueous dispersion and an oil-in-water type emulsion having a low viscosity and white color were obtained in the same manner as in Example 1 except that the stirring time in the second step was one minute.

Example 6

An aqueous dispersion and an oil-in-water type emulsion having a low viscosity and white color were obtained in the same manner as in Example 1 except that the stirring in the second step was performed at 500 rpm. The shearing speed in this stirring was about 1,500 s$^{-1}$2

Example 7

An aqueous dispersion and an oil-in-water type emulsion having a low viscosity in white color were obtained in the same manner as in Example 1 except that the stirring time in the first step was one minute.

Example 8

The oil-in-water type emulsion obtained in Example 1 was diluted twice with water and applied on an iron plate that has a metallic glossy smooth surface without any rust to form a coating film having a film thickness of 30 μm using a bar coater. This plate was subjected to outdoor exposure for one month to find that the plate without coating was greatly rusted on the surface, while the plate with coating maintained the initial metallic glossy surface.

Example 9

The oil-in-water type emulsion obtained in Example 1 was diluted twice with water and applied on a steel plate coated with an acrylic melamine resin, to form a coating film having a film thickness of 30 μm using a bar coater. When this plate was immersed in water for 1 week at room temperature, the resin swelled without the coating, while the initial state of the resin was maintained with the coating.

Example 10

Into a commercially available ultraviolet preventing makeup agent, 5% of the oil-in-water type emulsion obtained in Example 1 was charged, and after thoroughly stirring, a glass test piece was coated with the agent diluted twice with water using a bar coater at a thickness of about 30 After immersing the test piece in water at normal temperature for 1 hour, the SPF (sun protection factor) was measured. The SPF was reduced to 70% compared to the initial level without coating, whereas the SPF was reduced to 90% compared to the initial level with coating, which exceeded 80% the preferred level.

Comparative Example 1

Five grams of hydrophilic fumed silica ("Silica 1") was charged into a 500 mL stainless steel beaker. To this, 45 g of deionized water was added, and the mixture was stirred at 3,000 rpm for 2 minutes using an Ultraturrax™ mixer to obtain a silica aqueous dispersion.

Subsequently, 50 g of fluorine-containing organopolysiloxane having a viscosity of 1,000 mPa·s (available under the name of AF98/1000 from Wacker Chemie AG (Munich, Germany)) was charged, and the mixture was stirred at 1,500 rpm for 2 minutes. However, oil-in-water properties were not sufficient.

Comparative Example 2

An entirely white liquid was obtained in the same manner as Comparative Example 1 except that 5 g of hydrophobic fumed silica ("silica 2") was added instead of 5 g of hydrophilic fumed silica ("silica 1"). Oil-in-water properties in a state of being separated into an aqueous phase which was a continuous phase and an oil phase which was a dispersed phase was not sufficient.

Comparative Example 3

In a 500 mL stainless steel beaker, 2.5 g of hydrophilic fumed silica ("Silica 1") and 2.5 g of hydrophobic fumed silica ("Silica 2") were charged. Into this liquid, added was 45 g of deionized water, and the mixture was stirred at 500 rpm for 2 minutes using Ultraturrax to obtain a silica aqueous dispersion. The shearing speed in this stirring was about 1,900 $s^{-1}$.

Subsequently, 50 g of fluorine-containing organopolysiloxane having a viscosity of 1,000 mPa·s (available under the name of AF98/1000 from Wacker Chemie AG (Munich, Germany)) was charged, and the mixture was stirred at 1,500 rpm for 2 minutes to obtain an entirely white liquid. However, oil-in-water properties in a state of being separated into an aqueous phase which was a continuous phase and an oil phase which was a dispersed phase was not sufficient.

Comparative Example 4

As a first step, 50 g of fluorine-containing organopolysiloxane having a viscosity of 1,000 mPa·s (available under the name of AF98/1000 from Wacker Chemie AG) was charged in a 500 mL stainless steel beaker. To this, 45 g of deionized water was charged and the mixture was stirred at 1,900 rpm for 2 minutes by using an Ultraturraxm mixer to obtain an oil-in-water type emulsion. The shearing speed in this stirring was about 5,700 $s^{-1}$.

Subsequently, as a second step, 2.5 g of hydrophilic fumed silica ("silica 1") and 2.5 g of hydrophobic fumed silica ("silica 2") were charged, and stirred at 3,000 rpm for 2 minutes.

The shearing speed in this stirring was about 11,000 $s^{-1}$.

An entirely white liquid was obtained, but oil-in-water properties in a state of being separated into an aqueous phase which was a continuous phase and an oil phase which was a dispersed phase was not sufficient.

Comparative Example 5

Into a 500 mL stainless steel beaker, 2.5 g of hydrophilic fumed silica ("silica 1"), 2.5 g of hydrophobic fumed silica ("silica 2") and 50 g of fluorine-containing organopolysiloxane having a viscosity of 1,000 mPa·s (AF98/1000 from Wacker Chemie AG) were simultaneously charged. To this, 45 g of deionized water was added, and the mixture was stirred at 3,000 rpm for 2 minutes using an Ultraturrax™ mixer. The shearing speed in this stirring was about 11,000 $s^{-1}$.

An entirely white liquid was obtained, but oil-in-water properties in a state of being separated into an aqueous phase which was a continuous phase and an oil phase which was a dispersed phase was not sufficient.

TABLE 2

<Preparation Amounts and Production Conditions of Oil-In-Water Type Emulsions>

| | | Example 1 | Example 2 | Example 3 | Example 4 | Example 5 | Example 6 | Example 7 |
|---|---|---|---|---|---|---|---|---|
| Parts by Mass | Hydrophilic Dry Silica ("Silica 1") | 2.5 | 1 | 4 | | 2.5 | 2.5 | 2.5 |
| | Hydrophilic Dry Silica ("Silica 2") | 2.5 | 4 | 1 | | 2.5 | 2.5 | 2.5 |
| | Partially Hydrophobized Hydrophilic Dry Silica ("Silica 3") | | | | 5 | | | |
| | Water | 45 | 45 | 45 | 45 | 45 | 45 | 45 |
| | Flourine-Containing Organopolysiloxane (Wacker AF98/1000) | 50 | 50 | 50 | 50 | 50 | 50 | 50 |
| Molar Ratio of Surface Hydrophilic Groups/ Hydrophobic Groups In Entire Silica Particles At Raw Material Stage | | 50/50 | 26/74 | 74/26 | 70/30 | 50/50 | 50/50 | 50/50 |
| Charging Order | First Step | Silica | Silica | Silica | Silica | Silica | Silica | Silica |
| | Second Step | Oil | Oil | Oil | Oil | Oil | Oil | Oil |
| Sheering Speed ($s^{-1}$)/Stirring Time (min)(First Step) | | 11,000/2 | 11,000/2 | 11,000/2 | 11,000/2 | 11,000/2 | 11,000/2 | 11,000/1 |
| Sheering Speed ($s^{-1}$)/Stirring Time (min)(Second Step) | | 4,600/2 | 4,600/2 | 4,600/2 | 4,600/2 | 4,600/1 | 1,500/2 | 4,600/2 |

| | | Comparative Example 1 | Comparative Example 2 | Comparative Example 3 | Comparative Example 4 | Comparative Example 5 |
|---|---|---|---|---|---|---|
| Parts by Mass | Hydrophilic Dry Silica ("Silica 1") | 5 | | 2.5 | 2.5 | 2.5 |
| | Hydrophilic Dry Silica ("Silica 2") | | 5 | 2.5 | 2.5 | 2.5 |
| | Partially Hydrophobized Hydrophilic Dry Silica ("Silica 3") | | | | | |
| | Water | 45 | 45 | 45 | 45 | 45 |
| | Flourine-Containing Organopolysiloxane (Wacker AF98/1000) | 50 | 50 | 50 | 50 | 50 |
| Molar Ratio of Surface Hydrophilic Groups/ Hydrophobic Groups In Entire Silica Particles At Raw Material Stage | | 90/10 | 10/90 | 50/50 | 50/50 | 50/50 |
| Charging Order | First Step | Silica | Silica | Silica | Oil | Simultaneously Added |
| | Second Step | Oil | Oil | Oil | Silica | |
| Sheering Speed ($s^{-1}$)/Stirring Time (min)(First Step) | | 11,000/2 | 11,000/2 | 1,900/2 | 5,700/2 | 11,000/2 |
| Sheering Speed ($s^{-1}$)/Stirring Time (min)(Second Step) | | 4,600/2 | 4,600/2 | 4,600/2 | 11,000/2 | — |

TABLE 3

<Evaluation Results Of Oil-In-Water Type Emulsions>

| | | Example 1 | Example 2 | Example 3 | Example 4 | Example 5 | Example 6 | Example 7 |
|---|---|---|---|---|---|---|---|---|
| Oil-In-Water Type Emulsions | Oil-In-Water Properties | A | A | A | A | A | A | A |
| | Stability And Homogeneity | AA | AA | AA | AA | AA | AA | AA |
| | Particle Diameter (μm) | 15-20 | 15-20 | 15-20 | 15-20 | 15-20 | 15-20 | 15-20 |
| | Contact Angle Of Coated Film (90 Degrees Or More Is Considered Excellent In Water Repellency) | Excellent In Water Repellency | Excellent In Water Repellency | Excellent In Water Repellency | Excellent In Water Repellency | Excellent In Water Repellency | Excellent In Water Repellency | Excellent In Water Repellency |

TABLE 3-continued

<Evaluation Results Of Oil-In-Water Type Emulsions>

|  |  | Comparative Example 1 | Comparative Example 2 | Comparative Example 3 | Comparative Example 4 | Comparative Example 5 |
|---|---|---|---|---|---|---|
| Oil-In-Water Type Emulsions | Oil-In-Water Properties | C | C | C | C | C |
|  | Stability And Homogeneity | C | C | C | C | C |
|  | Particle Diameter (μm) | Unmeasurable | Unmeasurable | Unmeasurable | Unmeasurable | Unmeasurable |
|  | Contact Angle Of Coated Film (90 Degrees Or More Is Considered Excellent In Water Repellency) | Unmeasurable | Unmeasurable | Unmeasurable | Unmeasurable | Unmeasurable |

<Summary of Production Results of Aqueous Dispersions and Oil-in-Water Type Emulsions>

As shown in Tables 2 and 3, in a stage of the fumed silica as a raw material, when the ratio between the total number of moles of the surface hydrophilic groups of the entire particle groups obtained from each of the silica particle groups/the total number of moles of the surface hydrophobic groups of the entire particle groups obtained from each of the particle groups was in a range of 26/74 to 74/26, the stable aqueous dispersions and oil-in-water type emulsions were produced. However, when the molar ratio was 90/10, while the aqueous dispersion was stable, the stable oil-in-water type emulsion was not produced. When the molar ratio was 10/90, neither the aqueous dispersion nor the emulsion was stable.

Even if the molar ratio was 50/50, neither the aqueous dispersion nor the emulsion was stable with the low shearing speed.

When the shearing speed was sufficiently large, the variations in the degree of surface hydrophobicity at the secondary aggregate level became sufficiently small in both cases; however, when the shearing speed was not sufficient, the variations became large. It is speculated that the fluorine-containing organopolysiloxane as the oil was absorbed with the shearing speed that was significantly lower than that applied for producing the aqueous dispersion, and thus the self-micelle-like aggregates in the aqueous dispersion were shifted to the oil-in-water type emulsion (the Pickering emulsion) in almost the same state.

It was confirmed that the stable emulsion could not be produced by simultaneously mixing the silica, water, and the oil, or by mixing the silica after mixing water and the oil. Further, it was confirmed that it was enough to perform the primary shearing for the aqueous dispersion, and the auxiliary shearing for the emulsion. The formation of the self-micelle-like aggregates in the aqueous dispersion can be speculated on the basis of these observations.

It was confirmed that, for achieving the stability of the emulsion, the total molar ratio and variations thereof vary in accordance with the aggregating property of the silica.

It was confirmed that, regarding the shearing, considering that the rearrangement is required for the stability of the emulsion, although there is no restrictions on the shearing time as long as the shearing speed is at a predetermined level or higher, the shearing speed and the shearing time are involved in adjusting the specifications of the composite particles.

As describe above, it was confirmed that, even though the fluorine-containing organopolysiloxane having super water repellency or super oil repellency is used as the oil, the stable aqueous dispersion and the stable emulsion can be formed by adding the oil after the formation of the aqueous dispersion with almost the same conditions (the shearing conditions for forming the aqueous dispersion) used for the organopolysiloxane containing no fluorine. This finding has overthrown the conventional common general knowledge of a person skilled in the art.

<Discussion on Production of Self-Micelle-Like Aggregate>

(1) A fact that, in the oil-in-water type emulsion including the silica, water, and the oil, the stable oil-in-water type emulsion could be formed by adding the oil after the aqueous dispersion is formed by the silica and water, but the stable oil-in-water type emulsion could not be formed by simultaneously adding the silica, water, and the oil, or adding the silica after the oil and water are added.

(2) A fact that, when the oil is added after the aqueous dispersion is formed by the silica and water, the shearing at the predetermined shearing speed or more needs to be applied during the formation of the aqueous dispersion to form the stable and homogenous aqueous dispersion, while applying the shearing is not necessary to form the oil-in-water type emulsion by adding the oil to the stable and homogenous aqueous dispersion.

(3) A fact that the oil-in-water type emulsion can be formed by adding the oil after the aqueous dispersion is formed by the silica and water regardless of the types of the silica and the oil as the raw materials.

(4) A fact that the stable emulsion can be formed by bringing two parameters: the total mole number ratio represented by the total number of moles of the surface hydrophilic groups of the entire silica particle groups obtained from each of the silica particle groups/the total number of moles of the surface hydrophobic groups of the entire silica particle groups obtained from each of the silica particle groups; and the difference between the average value of the total mole number ratio and the molar ratio of the number of moles of the surface hydrophilic groups and the number of moles of the surface hydrophobic groups in each of the secondary particles constituting the silica particle group, within the predetermined ranges, and in this case, the solubility of the silica in water caused by the hydrophilic-rich aggregates predominantly existing in the silica particle group and the expression of the thixotropic property caused by the hydrophobic-rich aggregates predominantly existing in the silica particle group were reduced.

(5) A fact that the observation of the composite particle in the stable oil-in-water type emulsion using SEM shows that, on the surface of the composite particle, the surface of the oil drop is coated with the aggregated matters having a relatively spherical shape and a uniform size.

(6) A fact that, in the formed composite particle groups, variations in the particle diameter and the like between the composite particle groups are small and the specifications of the composite particles are affected by the shearing speed at the time of forming the aqueous dispersion.

From the above-described facts obtained in Examples, in forming the aqueous dispersion including the silica and water, when the fumed silica particle group forms the network due to the high aggregating property of the fumed silica particles, the stable oil-in-water type emulsion is formed by: applying the shearing at the predetermined shearing speed so as to form the aggregates which are not primarily constituted by the hydrophilic-rich aggregates or the hydrophobic-rich aggregates, while the fumed silica particle group forms the three-dimensional surrounding structure forming a space inside thereof instead of a planar structure; adjusting the total mole number ratio and the variations in the total mole number ratio; and adding the oil afterwards regardless of the types of the silica and the oil as the raw materials. Thus, in the meaning that applying the shearing induces the rearrangement between the silica aggregates and/or the orientation in the silica aggregates, thereby causing a high density of hydrophilicity on the outside and a high density of hydrophobicity on the inside, it can be inferred without doubt that the self-micelle-like aggregates are formed at the time of forming the aqueous dispersion.

The aqueous dispersion including the inorganic particles of the present invention is stable and homogenous and expresses functions of imparting the viscosity, the thixotropic property, and the like, thus reliability in the conventional applications such as modifying a coating material, a cosmetic, and various resins is significantly improved and new applications such as a functional coating material, a functional coating agent, an adhesive, and a sealant for construction can be developed. Further, the aqueous dispersion can be used as an intermediate for producing the stable and homogenous Pickering emulsion.

Further, in the oil-in-water type emulsion (the Pickering emulsion) of the present invention, the stability and homogeneity are very high, there is no limitations on the types of the oil, the homogeneity can be examined at the intermediate stage, the production is performed by the simple and low-cost method, and design for obtaining the stable and homogenous oil-in-water type emulsion can be performed. Thus, the reliability in the conventional applications can be significantly improved, and applications in a cosmetic with high functionality and applications in a new field requiring high requested characteristics and reliability such as an electronic material and an air bag can be expected.

When the composite particles of the oil-in-water type emulsion of the present invention are isolated, the stability and homogeneity are maintained, thus making it possible to provide the composite particles, which are easy to handle, have small variations in properties, and have high reliability. Thus, new applications in a cosmetic, additives for various resins, and the like can be expected. Further, the isolated composite particles can be returned to the emulsion again by adding water. Thus, significant improvements in costs in production storage and transportation can be expected as compared with the composite particles in the emulsion state, thereby causing tremendous impact on industries.

In the emulsion of the present invention, the fluorine-containing organopolysiloxane can be formed in a shape of coating film, granular material, or powder, which has been conventionally difficult. Thus, a base material can be imparted with water repellency, oil repellency, heat resistance, cosmetic performance, an antifouling property, weather resistance, a releasing property, long term stability, insulation, or a high dielectric constant. This enables various industrial applications such as protective coating and cosmetic applications, which have been conventionally difficult or insufficient, improvements of properties in general applications, and development of new applications.

Since the use of the organic surfactant can be omitted or reduced, an environmental problem accompanied by the use of the organic surfactant, the stable production of the emulsion, the stable state of the emulsion, and the emulsion being supplied with an aqueous system without the organic surfactant make the emulsion useful as a raw material of a cosmetic to be directly applied to the skin in terms of giving low stimulation or the like. Thus, the emulsion can be advantageously used in many industries.

REFERENCE SIGNS LIST

10 hydrophilic-rich primary aggregate
12 hydrophobic-rich primary aggregate
14 secondary aggregate
16 space
18 network structure
20 aqueous phase
22 oil phase
24 aggregate formed by fumed silica particle group

The invention claimed is:
1. A method for producing an oil-in-water emulsion, comprising the steps of:
 a) preparing a fumed silica at a secondary aggregate level by mixing a hydrophobic-rich fumed silica raw material in which surface silanol groups have been subjected to a hydrophobic treatment, with a hydrophilic-rich fumed silica raw material in which surface silanol groups remain, to form a composite mixture, the composite mixture having a ratio of all hydrophobic groups to all hydrophilic groups of from 80:20 to 20:80;
 b) producing an aqueous dispersion by adding the composite mixture obtained from step a) to water and shearing at a shearing speed which allows rearrangement of hydrophilic and hydrophobic lower order aggregates, the resulting aqueous dispersion containing fumed silica particles in which the lower order aggregates are aggregated with each other to form higher order aggregates aggregated by non-chemical bonds, thereby forming a network structure surrounding a hydrophobic space inside the network structure; and
 c) forming an oil-in-water emulsion by adding an oil to the aqueous dispersion produced in step b),
 wherein the oil-in-water emulsion comprises composite particles in which the oil is inside the network structure formed by the fumed silica particles at a secondary aggregate level, and
wherein the oil comprises a water and oil-repellant fluorinated polyorganosiloxane of an average composition:

$$R^1_a R^2_b SiO_{(4-a-b)/2} \qquad (1)$$

wherein the formula (1): where $R^1$ are the same or different from each other, and are substituted or unsubstituted, saturated or unsaturated monovalent hydrocarbon groups having 1 to 25 carbon atoms, substituted or unsubstituted aromatic groups having 6 to 30 carbon atoms, a hydroxyl group, alkoxy groups having 1 to 6 carbon atoms, or a hydrogen atom; $R^2$ are the same or different from each other, and are hydrocarbon groups which are saturated or unsaturated monovalent hydrocarbon groups having up to 25 carbon atoms, or aromatic groups having 6 to 30 carbon atoms, and in which hydrogen atoms bonded to carbon atom have been substituted with fluorine; b is a positive number which does not include 0; and a+b is 0.3 or more and less than 2.5.

2. The method of claim 1, further comprising a step of compounding the fumed silica particles at the secondary aggregate level with an organic surfactant so as to adjust a shape of the network-like surrounding structure before the step of producing the aqueous dispersion.

3. The method of claim 1, wherein the network structure includes a self-micelle aggregate in which a high density part of hydrophilic-rich lower order aggregates is in contact with an aqueous phase and a high density part of hydrophobic-rich lower order aggregates is in contact with other hydrophobic-rich lower order aggregates to form a hydrophobic space surrounding the oil inside the self-micelle aggregate.

4. The method of claim 2, wherein the step of compounding the fumed silica particle group at the secondary aggregate level and the organic surfactant includes a step of predetermining a compounding ratio so as to adjust a binding property of the self-micelle aggregates to oil drops surrounded by the self-micelle aggregates.

5. The method of claim 1, wherein step a) of preparing the fumed silica particle group at the secondary aggregate level includes a step of mixing a hydrophobic-rich fumed silica raw material and a hydrophilic-rich fumed silica raw material by setting a total mole number ratio represented by a total number of moles of surface hydrophilic groups of the entire fumed silica particle groups obtained from each of the fumed silica particle groups/a total number of moles of surface hydrophobic groups of the entire fumed silica particles obtained from each of the fumed silica particles to a predetermined range so as to adjust a ratio of the self-micelle aggregates.

6. A method for forming a coating comprising the method of claim 1 wherein step b) additionally comprises applying the aqueous dispersion to a substrate.

* * * * *